(12) United States Patent
Papazoglou et al.

(10) Patent No.: US 8,812,083 B2
(45) Date of Patent: Aug. 19, 2014

(54) METHODS OF OPTICALLY MONITORING WOUND HEALING

(75) Inventors: Elisabeth S. Papazoglou, Yardley, PA (US); Leonid Zubkov, Philadelphia, PA (US); Michael T. Neidrauer, Drexel Hill, PA (US); Linda Zhu, Newtown, PA (US); Kambiz Pourrezaei, Gladwyne, PA (US); Michael S. Weingarten, Penn Valley, PA (US)

(73) Assignees: Philadelphia Health & Education Corporation, Philadelphia, PA (US); Drexel University, Philadelphia, PA (US)

( * ) Notice: Subject to any disclaimer, the term of this patent is extended or adjusted under 35 U.S.C. 154(b) by 462 days.

(21) Appl. No.: 12/937,590

(22) PCT Filed: Apr. 21, 2009

(86) PCT No.: PCT/US2009/041232
§ 371 (c)(1),
(2), (4) Date: Dec. 22, 2010

(87) PCT Pub. No.: WO2009/131989
PCT Pub. Date: Oct. 29, 2009

(65) Prior Publication Data
US 2011/0124987 A1    May 26, 2011

Related U.S. Application Data

(60) Provisional application No. 61/046,640, filed on Apr. 21, 2008, provisional application No. 61/054,535, filed on May 20, 2008.

(51) Int. Cl.
*A61B 6/00* (2006.01)
(52) U.S. Cl.
USPC ................. 600/473; 600/475; 600/477

(58) Field of Classification Search
USPC ............................. 600/473, 475, 476, 477
See application file for complete search history.

(56) References Cited

U.S. PATENT DOCUMENTS

2002/0084417 A1    7/2002    Khalil et al.
2002/0173706 A1    11/2002   Takatani

OTHER PUBLICATIONS

Weingarten, M. S., Measurement of optical properties to quantify healingof chronic diabetic wounds, Wound Rep Reg 14, 364-370 (2006).*

(Continued)

*Primary Examiner* — Rajeev Siripurapu
(74) *Attorney, Agent, or Firm* — Pabst Patent Group LLP

(57) ABSTRACT

Optical changes of tissue during wound healing measured by Near Infrared and Diffuse Reflectance Spectroscopy are shown to correlate with histologic changes. Near Infrared absorption coefficient correlated with blood vessel in-growth over time, while Diffuse Reflectance Spectroscopy (DRS) data correlated with collagen concentration. Changes of optical properties of wound tissue at greater depths are also quantified by Diffuse Photon Density Wave (DPDW) methodology at near infrared wavelengths. The diffusion equation for semi-infinite media is used to calculate the absorption and scattering coefficients based on measurements of phase and amplitude with a frequency domain or time domain device. An increase in the absorption and scattering coefficients and a decrease in blood saturation of the wounds compared to the non wounded sites was observed. The changes correlated with the healing stage of the wound. The methodologies used to collect information regarding the healing state of a wound may be used to clinically assess the efficacy of wound healing agents in a patient (e.g., a diabetic) and as a non-invasive method to detect the progress of wound healing, particularly chronic wounds due to diabetes. The methodology applies to ischemic environments, impaired healing states, and emerging subsurface tissue deterioration, such as in pressure ulcers, venous ulcers, and ubiquitous ulcers.

10 Claims, 30 Drawing Sheets

(56) References Cited

OTHER PUBLICATIONS

Weingarten, M.S., Correlation of near infrared absorption and diffuse reflectance spectroscopy scattering with tissue neovascularization and collagen concentration in a diabetic rat wound healing model, Wound Rep Reg, 16, 234-242 (2008). (noting an earlier published online date than that submitted by Applicant on their IDS).*

Papazoglou, E.S., Optical Properties of Wounds: Diabetic Versus Healthy Tissue, IEEE Transactions of Biomedical Engineering, vol. 53, No. 6, (Jun. 2006).*

Khaodhiar, L., The Use of Medical Hyperspectral Technology to Evaluate Microcirculatory Changes in Diabetic Foot Ulcers and to Predict Clinical Outcomes, Diabetes Care, vol. 30, No. 4, (2007).*

Rajbhandari, S., Early Identification of Diabetic Foot Ulcers That May Require Intervention Using the Micro Lightguide Spectrophotometer, Diabetes Care, vol. 22, No. 8, (1999).*

Schmidt, W. D., Contact-Free Spectroscopy of Leg Ulcers: Principle, Technique, and Calculation of Spectroscopic Wound Scores, Journal of Investigative Dermatology, vol. 116, No. 4, 531-535 (2001).*

PCT Application No. PCT/US2009/041232 : International Search Report and Written Opinion of the International Searching Authority, Dec. 23, 2009, 10 pages.

Weingarten et al., "Correlation of Near Infrared Absorption and Diffuse Reflectance Spectroscopy Scattering With Tissue Neovascularization and Collagen Concentration in a Diabetic Rat Wound Healing Model", Wound Repair and Regeneration, Mar.-Apr. 2008, 16(2), 234-242.

* cited by examiner

METHODS OF OPTICALLY MONITORING WOUND HEALING

CROSS-REFERENCE TO RELATED APPLICATIONS

This application is the National Stage of International Application No. PCT/US2009/041232, filed Apr. 21, 2009, which claims the benefit of U.S. Provisional Application No. 61/046,640 filed Apr. 21, 2008 and U.S. Provisional Application No. 61/054,535, filed May 20, 2008, the disclosures of which are incorporated herein by reference in their entirety.

GOVERNMENT INTEREST

This invention was made with government support under contract W81XWH-06-1-0742 awarded by the US Army Medical Research and Materiel Command/TATRC. The government has certain rights in the invention.

FIELD OF THE INVENTION

The invention relates to methods for measuring changes in optical properties of tissue during acute wound healing and, more particularly, to the use of diffuse photon density wave (DPDW) methodology at near infrared frequencies to calculate the absorption and scattering coefficients of wound tissue based on measurements of phase and/or amplitude with a continuous wave, a frequency domain, or a time domain near infrared device. The invention also relates to determining whether a wound is healing by assessing tissue neovascularization and collagen concentration in a wound by correlating measurements made using near infrared absorption and diffuse reflectance spectroscopy scattering and by monitoring changes in oxygenated hemoglobin over time. The invention applies to subsurface tissue optical properties and oxygenation and relates to ischemic environments, impaired healing states, and emerging wounds such as pressure or ubiquitous ulcers.

BACKGROUND OF THE INVENTION

Assessment of healing in chronic wounds is gaining importance as new and expensive wound treatments are brought to market. A wide variety of chronic wound treatments such as topical growth factors, bioengineered skin equivalents, negative pressure wound therapy, and hyperbaric oxygen therapy are commercially available and clinical studies of these products have shown some evidence of improved healing compared to standard of care. However, the effectiveness of each treatment is not the same in all patients, so rapid and accurate evaluation of healing progress in each individual is critical so that unsuccessful treatments can be discontinued and alternate treatments initiated as soon as possible. Reliable methods of evaluating wound healing would benefit both wound clinics by reducing the duration and cost of treatment, and the wound research community in the evaluation of clinical trials.

The main limitation of traditional wound evaluations is that they can give information mostly from the surface of the wound. Such surface characteristics of a wound do not take into account the health of the wound environment beneath the surface in the whole wound bed, and provide inadequate information regarding the wound healing status of a wound. Therefore, misdiagnosis may occur or treatment may not be altered as early as possible, with direct implications on the quality and cost of care for chronic wounds. For example, image analysis of wound pictures for color or texture pertains strictly to surface information and optical methods such as Diffuse Reflectance Spectroscopy (DRS) or Optical Coherence Tomography (OCT) can penetrate to only approximately 1 millimeter. Non-invasive analysis of the full depth of the chronic wound bed could provide the clinician with a more complete picture of wound health, allowing better prediction of wound closure and wound recurrence than can be achieved by surface measurements alone.

Several human studies have been conducted in an attempt to non-invasively characterize tissue beneath the surface of chronic wounds. High frequency ultrasound (HFUS) at frequencies in the range of 20 MHz permits high resolution (microscopic-level) imaging of skin at depths of up to 2 cm. A preliminary study showed that HFUS could be used to image structural features beneath the surface of human chronic wounds and qualitative comparisons were made with healthy skin. HFUS was used to measure skin thickness in several types of human chronic wounds (diabetic, venous, pressure, and ubiquitous ulcers), and a later study by Dyson et al. described in "Wound healing assessment using 20 MHz ultrasound and photography," Skin Research and Technology, 2003, Vol. 9, pages 116-121, demonstrated the use of HFUS to calculate the width and depth of small acute wounds that were created experimentally in human subjects. However, it is unclear how this method would translate to chronic wounds that are very different in shape, size, and also have more ambiguous boundaries than acute wounds.

Optical Coherence Tomography (OCT) is a non-invasive imaging modality that uses low coherence interferometry to create high resolution cross-sectional images of structural features in human skin at depths of up to 1.2 mm. This method has not yet been used to image human wounds, but structures visible in OCT images of experimentally-created animal wounds have been qualitatively correlated to histological micrographs of the same wounds, and an automated imaging algorithm was developed to calculate the size of these acute animal wounds. In another animal study, polarization-sensitive OCT was used to monitor temporal changes in collagen birefringence during healing, and measurements of birefringence were shown to be greater in chemically accelerated wound healing as compared to chemically impaired healing. As with HFUS, the clinical utility of OCT as a wound monitoring methodology is uncertain due to the size and complexity of human chronic wounds.

Laser Doppler Flowmetry (LDF) and its modified methodology of Laser Doppler Imaging (LDI) are optical methods that rely on frequency shifts of an incident light beam (typically a laser in the near infrared wavelength range) to determine a quantitative index that is related to the average velocity and number of red blood cells within a tissue volume. Some researchers have used LDF and LDI to quantify relative values of cutaneous blood flow in human chronic wounds. These studies identified regions of increased blood flow within chronic wounds that may correlate to granulation tissue; however, changes in blood flow were not monitored over time. The clinical utility of LDF and LDI for serial assessment of chronic wounds is limited due to low penetration depths (~1-2 mm) and issues with light reflection caused by curvature of the feet and presence of moisture on the surface of the wound.

Diffuse Reflectance (or Remittance) Spectroscopy (DRS) is an optical method that uses light at visible and near infrared wavelengths (400 to 1500 nm) to measure hemoglobin concentration and oxygenation of blood in superficial capillaries, to depths of approximately 1 mm. DRS spectra from chronic leg ulcers (both venous and arterial) have been empirically correlated to qualitative wound scores assessed by physicians, and changes in oxygen saturation were measured over the course of healing using DRS in diabetic foot ulcers. However, changes of the surface appearance due to bleeding and other reasons will significantly affect the capability of DRS to provide on its own information about the wound status and oxygenation.

Generally speaking, the determination of wound surface area is highly inaccurate and subjective. (See Robson, M. C., et al., *"Wound Healing Trajectories as Predictors of Effectiveness of Therapeutic Agents,"* in Archives of Surgery. 2000, Am Med. Assoc. p. 773-777). Wound edges may be hard to determine because of complex wound geometry. Width and depth measurements may vary from between observers during the same clinic session and are highly inaccurate between visits. Surface area does not take into account changes in wound volume. Ultrasound measurements and image analysis of digital photos provide more accurate information but are difficult to use in a busy clinical setting.

In previous publications of the present inventors, it has been reported that near infrared optical measurements correlated with wound area reduction and were able to distinguish between a diabetic wound and a non-diabetic wound in a rat model. Weingarten, M. S., et al., "Measurement of optical properties to quantify healing of chronic diabetic wounds," Wound Repair and Regeneration, 2006, Vol. 14(3): pp. 364-370. As will be explained herein, the inventors have expanded upon this research by combining Near Infrared (NIR) with Diffuse Reflectance spectroscopy (DRS) and reporting whether the near infrared absorption coefficient correlates with histological changes in the wounds and whether the DRS scattering function correlates with collagen concentration in the healing tissue.

Moreover, it is established that wounds, burns and lesions need oxygen to heal and that ischemic conditions represent impaired healing environments. Therefore, by measuring oxygenated hemoglobin, deoxygenated hemoglobin, and oxygen saturation, the inventors suggest that it is possible to predict wound healing. Current methods in clinical wound care practice rely on estimates of the surface area by measuring length and width of the lesion. These methods are highly subjective and more importantly cannot assess the probability of wound healing in impaired environments, such as in chronic wounds due to diabetes, venous ulcers, pressure ulcers, ubiquitous ulcers, and others. Invasive monitoring based on biopsies could provide information about the physiology and biochemistry of healing but is invasive and impractical, while monitoring based on wound fluid is controversial due to debates over appropriate correlation of wound fluid composition to wound tissue.

At present, various optical methods have been proposed and can be used for determining parameters representing skin injury or for monitoring the healing processes. Most optical methods are non-invasive and relatively inexpensive and as such offer major advantages compared to invasive methods. Different modifications of diffuse reflectance spectroscopy (DRS) have become the most common methodology in monitoring wounds, burns and lesions. DRS has been used extensively for evaluating skin changes at superficial depths up to 1 mm because with a typical broad range wavelengths source of incident light (400-1500 nm) the strong absorption exhibited by the tissue inhibits optical probing of deeper layers. Using specialized algorithms to fit DRS re-emission spectra to phantoms and model systems, many investigators obtained important information about the depth of burn injuries, sun damage, topical drug delivery, and water content of the skin.

In wound characterizations, the absence of significant depth penetration makes DRS data difficult to interpret. For example, DRS data from a significant number of wounds had to be collected in order to develop an empirical algorithm that could mimic a clinical wound assessment score which averages clinical observations. In order to probe deeper tissue depths with optical non-invasive methods, a different approach than DRS is desired. Such an approach is described herein.

SUMMARY OF THE INVENTION

The inventors have found that changes in blood vessel in-growth and/or ischemia in a wound may be quantified using near infrared (NIR) measurements and that the collagen concentration may be quantified using diffuse reflectance spectroscopy (DRS) measurements in the wound tissue. The NIR scattering coefficient was found to not correlate with collagen concentration or cell count, but to correlate to vessel organization, possibly due to the depth of tissue probed. Because of the penetration depth and the wavelength used in DRS, blood vessel organization and presence of neutrophils is less a factor in DRS scattering as compared to collagen. These two methods therefore were found to provide complementary information.

Differences in the change of the absorption coefficient during the wound healing period were found, and in control wounds, the rate of change in absorption coefficients was consistently higher at 685 nm and 830 nm compared to impaired (e.g., diabetic) wounds. This is the exact behavior predicted by vessel in growth in the control as blood vessel growth in the control proceeded more rapidly. The scattering function determined by DRS was also found to correlate very well with collagen concentration determined by trichrome staining in both the impaired and control wounds.

In part to take advantage of these observations, a method of collecting information regarding the healing state of a wound is provided. In an exemplary embodiment, the method includes illuminating wound tissue with light from a light source, measuring the amplitude and/or phase shift of the light as it propagates through the wound tissue, calculating an optical absorption coefficient and/or a reduced scattering coefficient using the measured values, and correlating collagen concentration in the wound tissue with the reduced scattering coefficient calculated from measured parameters and/or correlating blood vessel in-growth and/or ischemia in the wound tissue with the optical absorption coefficient using the measured values. Changes in collagen concentration over time may be determined from changes in the reduced scattering coefficient over time. Similarly, changes in blood vessel in-growth and/or ischemia over time may be determined from changes in the optical absorption coefficient over time. The light is preferably provided by a laser and transmitted at a near infrared wavelength such as of 650-870 nm. The light may also be transmitted at specific near infrared wavelengths such as 685 nm, 780 nm, 830 nm, and/or 950 nm. The light output by the laser may be modulated to produce a diffuse photon density wave (DPDW) in the wound tissue. On the other hand, the light may be used to differentiate an impaired wound (e.g., chronic wounds such as diabetic, pressure ulcer, venous ulcer, ubiquitous ulcer, and ischemic wounds) from a non-impaired wound (normally healing wound) by measuring changes in blood vessel in-growth and/or ischemia in the wound over time and correlating optical absorption coefficients obtained from the wound over time with blood vessel in-growth and/or ischemia seen histologically for impaired and control wounds. In embodiments, the method may include detecting pressure ulcers or venous ulcers in the wound from changes in the optical absorption coefficients over time.

The method described herein further includes measuring the size of the wound by calculating wound surface area and measuring a healing rate of the wound by calculating the difference between the surface area of the wound at different points in time and dividing the difference by the original surface area of the wound.

In an exemplary embodiment, correlating the collagen concentration in the wound tissue with the reduced scattering coefficient includes correlating an increase in a diffuse reflectance spectroscopy scattering function obtained over time in the wound with an increase in collagen during healing of the wound. In an exemplary embodiment, the collagen concentration in the wound may be measured using DRS measurements over time.

The illuminating and measuring steps may be performed using a continuous wave, frequency domain, or time domain measurement device that does not contact the wound. In this embodiment, the calculation of the absorption and/or reduced scattering coefficients and a quantification of blood oxygenation is performed using a diffusion equation for semi-infinite media.

In accordance with another aspect of the method, monitoring changes in oxygenated hemoglobin over time provides as an indication of whether the wound is healing. The changes in oxygenated hemoglobin may be quantified by calculating a rate of change and variability in optical absorption coefficient and hemoglobin concentration over time.

BRIEF DESCRIPTION OF THE DRAWINGS

The above-mentioned and other features and advantages of the invention will become apparent from the following detailed description in connection with the accompanying drawings, of which.

DETAILED DESCRIPTION OF ILLUSTRATIVE EMBODIMENTS

Figure 1:
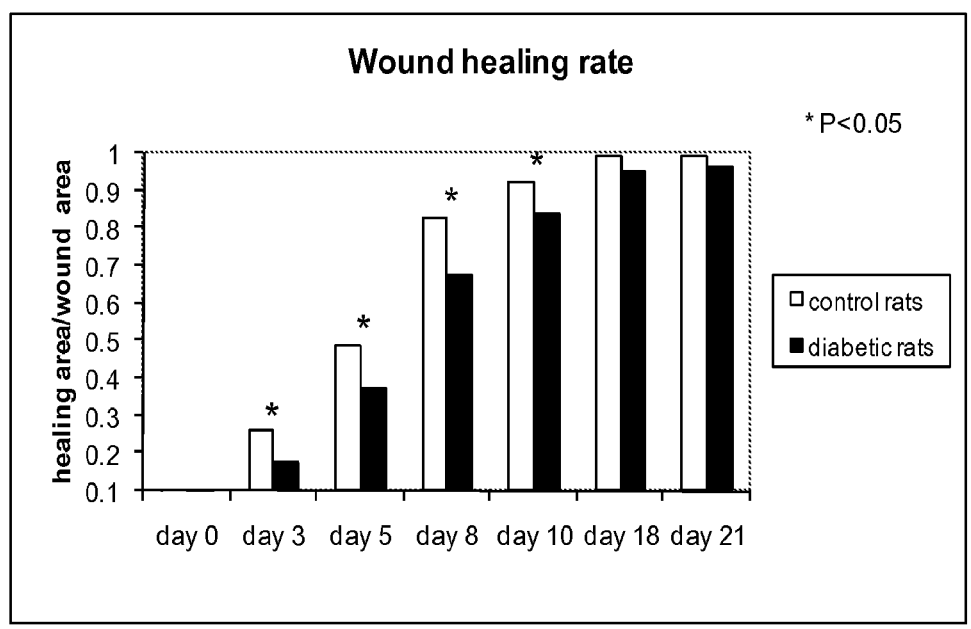
FIG. 1 illustrates the rate of wound healing in diabetic and control rats, as calculated from image analysis of digital photographs of the wounds.

A detailed description of illustrative embodiments of the present invention will now be described with reference to FIGS. 1-36. Although this description provides a detailed example of possible implementations of the present invention, it should be noted that these details are intended to be exemplary and in no way delimit the scope of the invention.

Monitoring Surface of Wound to Collect Data Regarding Healing State of Wound

Material and Methods

A frequency domain diffuse optical tomography instrument developed by the School of Biomedical Engineering at Drexel University was used to non-invasively measure the optical properties of tissue at depths up to several millimeters. The instrument includes four laser diodes (685, 785, 830, and 950 nm) controlled by an optical switch, four avalanche photodiode detector channels, and a radio-frequency (RF) generator that modulates the laser output at a frequency of 70 MHz. The device measures the amplitude and phase shift of light as it propagates through tissue, and uses a diffusion-based model to calculate the optical absorption coefficient ($\mu_a$) and reduced scattering coefficient ($\mu'_s$). A fiber optic probe delivers light through a single optical fiber and collects light through four optical fibers spaced at distances of 4 mm to 16 mm from the source fiber. The instrument was calibrated and its stability determined using intralipid solutions of varying concentration and therefore varying scattering and absorption coefficients. During the described measurements, the instrument was calibrated with solid phantoms. Details of this instrument have been published previously by Weingarten, M. S., et al. in "Measurement of optical properties to quantify healing of chronic diabetic wounds," Wound Repair and Regeneration, 2006, Vol. 14(3): pp. 364-370. As those skilled in the art will appreciate, chromophores in the wound that absorb light delivered at these wavelengths are primarily oxy and deoxyhemoglobin and water.

Experimental Animal Model:

An animal model consisting of hairless rats, made diabetic by intraperitoneal Streptozotocin (STZ) administration, was used. In particular, the animal model chosen was the hairless female rat. During the course of the study, animals were housed in individual cages on alpha cellulose bedding and maintained in an animal care facility with a 12 hour light and dark cycle. Food and water were supplied ad libitum.

Thirty, ten week old Sprague-Dawley female hairless rats, weighing approximately 205 g, were acquired. Baseline near infrared data were collected on all rats for 14 days. Eighteen rats were rendered diabetic using intraperitoneal injection of STZ at 75 mg/kg. Twelve rats were maintained as the control group. In order to assure successful induction of diabetes, blood glucose levels were monitored in diabetic rats. On day 36, a full thickness wound of 4.6 cm$^2$ was made using sterile technique in an animal surgical suite. One wound was inflicted on the left side of the dorsal area of each animal. The right side of each animal was left unwounded to provide a control site and to enable assessment of any systemic changes in optical properties connected to either diabetes or the wound. The surgery was performed using isoflurane anesthesia administered via a face mask. All wounds were covered with a Tegaderm (3M, Minneapolis, Minn.) sterile transparent dressing. After surgery all rats were fitted with "Elizabethan" type collars to prevent them from scratching their wounds. Blood sugar and weight were checked weekly in the rats.

Optical Measurement of Wound

Near Infrared Spectroscopy (NIR)

NIR optical measurements were performed on 2 locations of the wound side (center of the wound and peri-wound), and on one location on the control (right) side. Before measuring, pooled blood or fluid in the wound was removed with gauze. Optical data were collected from the peri-wound area, the wound center, and the symmetrical unwounded right side (control side). Each position was measured three times to ensure reproducibility. The data reported reflect the average of these three measurements and standard error was less than 2%. Measurement of the wounds using the near infrared instrument was performed twice weekly.

The optical device was calibrated before each experiment. The choice of wavelengths including 680-870 nm allowed assessment of the predominant chromophores in the wound oxy and deoxyhemoglobin. The addition of the 950 nm wavelength allowed determination of water concentration in the wound and therefore the state of dehydration of the tissues. The lasers were modulated at 70 MHz to produce a diffuse photon density wave (DPDW) in the tissue. Appropriate algorithms convert the amplitude and phase at these four wavelengths into measurement of tissue absorption and scattering. Since tissue is a very strong scattering medium with light being scattered at every 1 mm of tissue, an approximation of DPDW was used to calculate the coefficients of absorption and scattering. The probe interrogated the tissue at a depth of approximately 3-5 mm.

Diffuse Reflectance Spectroscopy (DRS)

A diffuse reflectance spectroscopy (DRS) instrument was used to measure the intensity of backscattered light at a depth between 100-300 microns from the skin/wound surface. The instrument consisted of a Tungsten light source (Ocean Optics, Boca Raton, Fla.), a bifurcated fiber bundle (Multimode Fiber Optics, East Hanover, N.J.), a spectrophotometer (Ocean Optics, Boca Raton, Fla.) and an analyzer. Light was delivered to the skin by one leg of the fiber bundle connected to the light source and collected by the other leg connected to the spectrophotometer. A fiber optic probe consisting of 600 randomly mixed optical fibers with 50 μm core diameter was slightly placed on the skin. The total probe size is about one half inch in diameter and the active area of the probe is about 2 mm in diameter. A reflectance spectrum was acquired between 400 nm and 750 nm. The DRS scattering function was calculated by finding the intercept at 630 nm of a straight line fitted to the intensity data between 630 nm and 700 nm using a linear least squares fitting algorithm. A similar function was used by Knoefel, W. T., et al. in "Reflectance spectroscopy of pancreatic microcirculation," *Journal of Applied Physiology*, 1996, Vol. 80(1), pp. 116-123, to represent a measure of the scattering intensity.

In vitro measurements of collagen phantoms were performed with DRS to assess the sensitivity of the method in determining collagen concentration. Three collagen type I gel phantoms, each approximately 1 cm thick were made. Collagen gels were prepared from rat tail type I high concentration collagen (BD science, CA) in standard 6-well plates by following the recommended manufacturer's protocol. Briefly, collagen was dissolved in water to the desired concentration (3 mg/ml, 4.5 mg/ml, and 6 mg/ml). Phosphate buffered saline and 1N NaOH were added to provide physiological pH and ionic strength. The collagen was allowed to gel at 37 degrees C. for about 20-30 minutes.

Determination of Wound Size

Measurements of wound size were determined by calculating wound surface area. This was determined using cross polarization digital photographs taken at the same time the near infrared data were collected. The image analysis tool IMAGE PRO (Media Cybernetics, Silver Spring, Md.) was used to calculate the area of each wound. As these wounds were of uniform depth, wound volume was not calculated. Near infrared spectroscopy, DRS, and digital photography were performed with the rats receiving inhaled isoflurane anesthesia so as to avoid motion artifacts.

Wound Biopsies

With the rats receiving inhaled isoflurane anesthesia, rats in the diabetic group and in the control group had complete excision of their wounds and the area of the dorsum contralateral to the wound on day 5 and 10, and 21 after wounding. These rats were then sacrificed. Wound excision was performed on 3 control rats and 6 diabetic rats on day 5, and 3 control rats and 6 diabetic rats on day 10. Excisional biopsies were performed on 6 control rats and 4 diabetic rats on day 21. A total of 28 wounds and 28 control areas were excised and examined histologically.

Hematoxylin and eosin staining was performed in order to observe tissue structure and cell morphology. Briefly, after rehydration, slides are immersed in Hematoxylin solution for 3 minutes, and then washed with tap water for 5 minutes, immersed with Eosin solution for 1 minute and dehydrated with xylene.

Lectin staining (a sugar binding protein of non-immune origin that agglutinates cells or precipitates glycoconjugates) was used to stain vessels in the tissue, and visualize vascularization. Lectin can be used as a marker of angiogenesis because it binds to endothelial cells reveals the overall vascular architecture. Briefly, sections were washed in 1×PBS for 10 minutes after rehydration. Sections were stained with Alexa Fluor 488 conjugated lectin (Invitrogen L2-1415) for 30 minutes in the dark with a concentration at 1:250 and washed with 1×PBS 3 times for 5 minutes each. Determination of microvessel density was performed as described by Weidner et al in "Tumor angiogenesis and metastasis—correlation in invasive breast carcinoma," in New England Journal of Medicine, 1991, pp. 1-8. Vessel counts were assessed by light microscopy in areas of the wound tissue containing the highest number of positive lectin areas visualized at low power. The six highest areas of vascularity which did not overlap were identified, a vessel count performed, and the average of the six counts calculated.

The same procedure as that followed for lectin staining was used for DAPI (4',6-diamidino-2-phenylindole) (visualize nuclear DNA) but with an additional step. This step involved mounting sections with VECTASHIELD® and DAPI Mounting Medium. Vessels were stained as fluorescent green and cell nuclei were stained as fluorescent blue. Image analysis of DAPI stained fluorescence images (3-5 images per sample) was performed in order to assess the number of cells, as described by Otto, F. in "DAPI staining of fixed cells for high-resolution flow cytometry of nuclear DNA," *Methods Cell Biol*, 1990. Col. 33, pp. 105-10.

Collagen fibers were visualized by Gomori's trichrome staining method as described by Gomori, G. in "Aldehyde-fuchsin: a new stain for elastic tissue," *Am J Clin Pathol*, 1950, Vol. 20(7), pp. 665-6. Trichrome is an acidic dye that selectively stains collagen and is the standard method used in pathology labs. The image analysis software Image Pro was used to determine the concentration of collagen by counting the pixel intensity of collagen in a given area.

Results

Wound Size

In the 30 wounds measured during the 21 day period after wounding, wound size in the control group decreased at a faster rate when compared to the diabetic group (FIG. 1). Healing rates were calculated according the formula:

Percent Healing=(Original wound area−wound area)/(original wound area)

A statistically significant ($p<0.05$) difference between the percent healing of diabetic and control rats was found using the Student t-test. These results duplicated the healing rates observed by this group in Weingarten, M. S., et al., "Measurement of optical properties to quantify healing of chronic diabetic wounds," *Wound Repair and Regeneration*, 2006, Vol. 14(3), pp. 364-370.

Wound contraction, was defined as:

Wound contraction=(wound area)/(original wound area).

Figure 2:
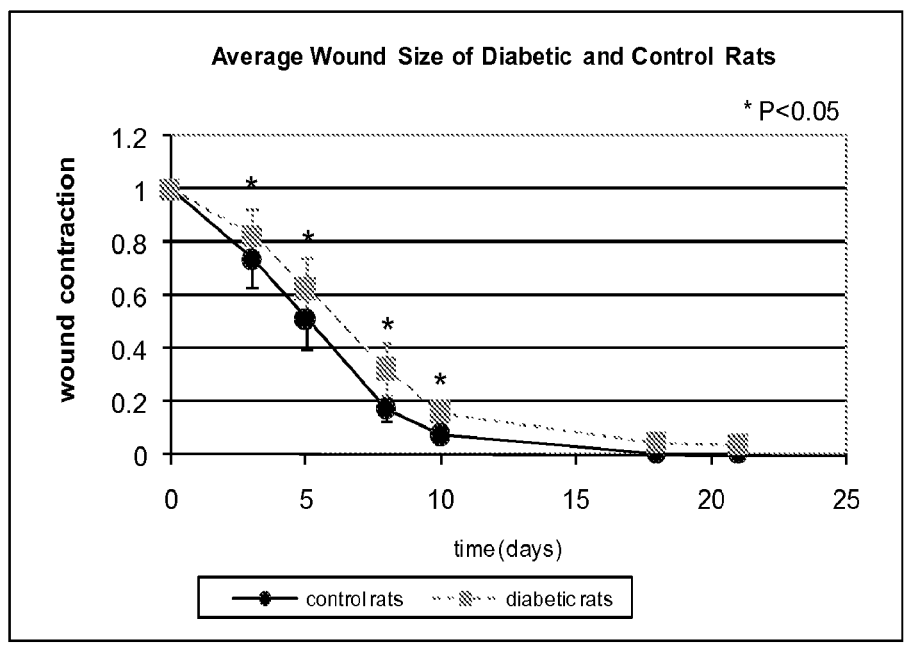
FIG. 2 illustrates wound contraction in diabetic and control rats, as calculated from image analysis of digital photographs of the wounds.

As illustrated in FIG. 2, wound contraction in the control group occurred at a faster rate than the diabetic.

Near Infrared Absorption Data ($\mu_a$)

Figure 3:
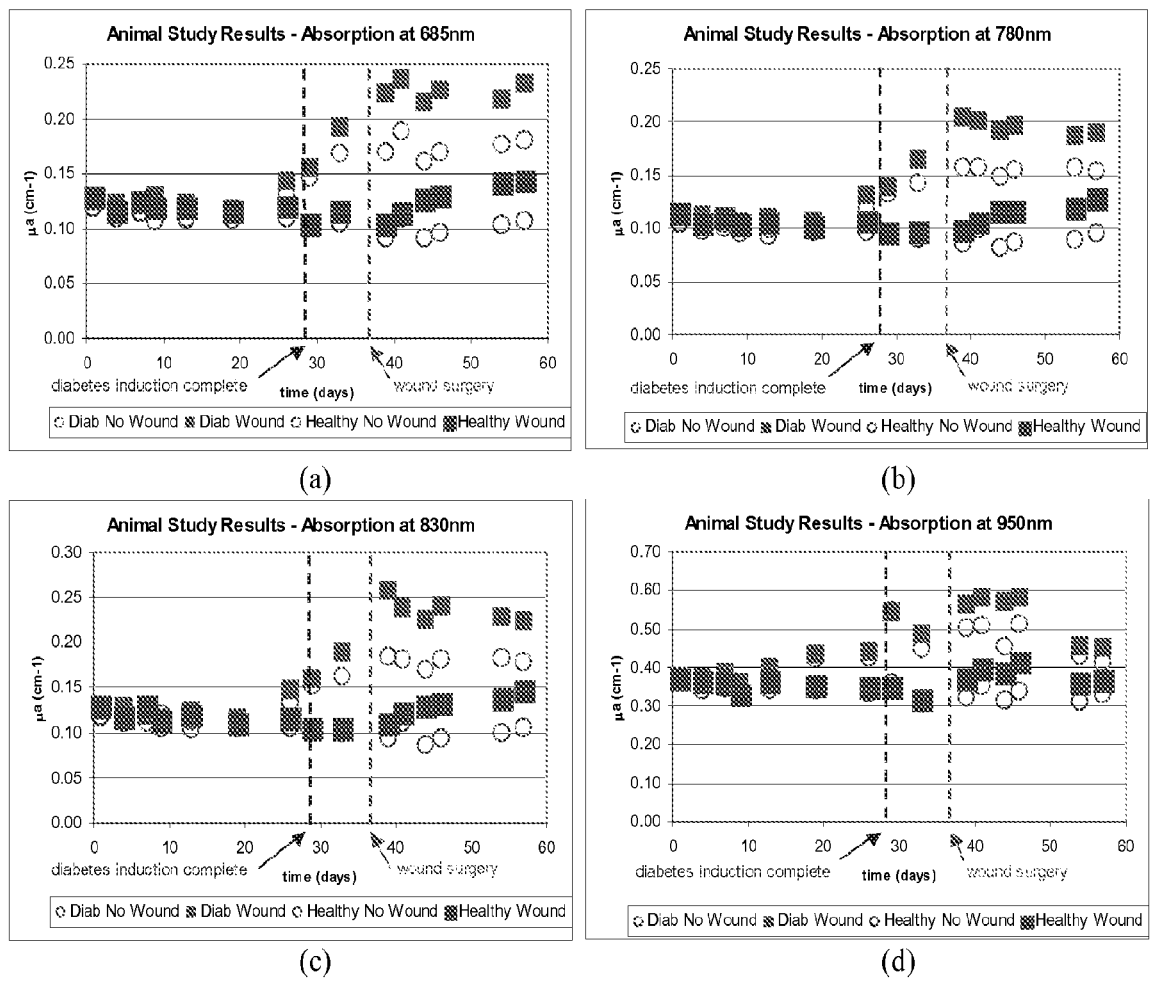
FIG. 3 illustrates the average absorption coefficient ($\mu_a$) in diabetic non-wound tissue, diabetic wounds, healthy non-wound tissue, and healthy wounds at (a) 685 nm, (b) 780 nm, (c) 830 nm, and (d) 950 nm.

Absorption coefficients increased in the diabetic rats starting soon after the induction of diabetes. Absorption coefficients increased within days of wounding in the diabetic wounds compared to the controls. As illustrated in FIG. 3, the average absorption coefficients were significantly higher in the diabetic wounds when compared to the diabetic non-wounded side and to the controls over the time of healing.

Figure 4:
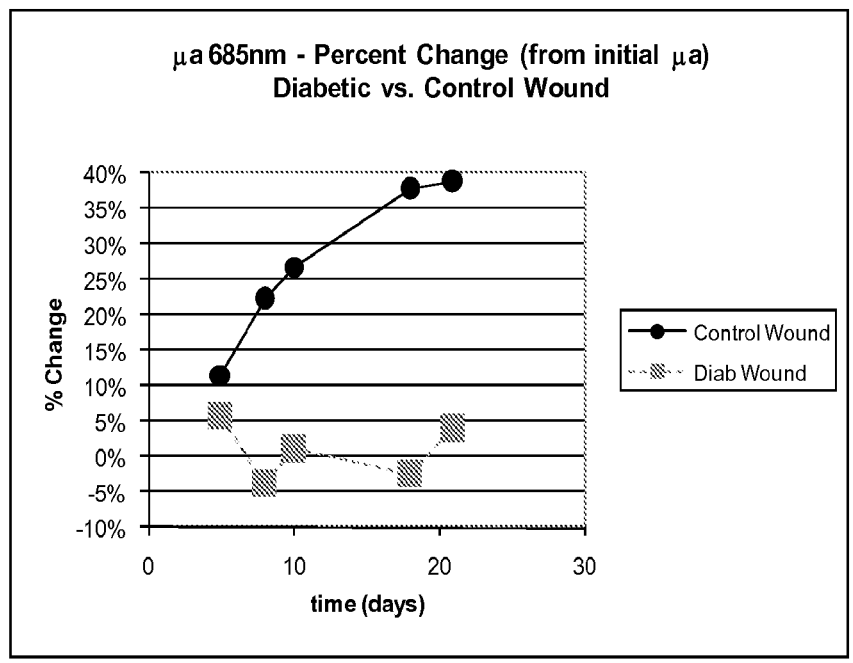
FIG. 4 illustrates the percent change of absorption coefficients ($\mu_a$) at 685 nm in diabetic vs. control wounds, showing that similar results were obtained for all wavelengths.

As illustrated in FIG. 4, the percent change in absorption coefficients ($\mu_a$) in the control wounds was greater than the percentage change in $\mu_a$ in the diabetic wounds starting from the time of wounding. Percent change was calculated using the following formula:

$$\% \text{ change} = \frac{\mu_a - \mu_a^{init}}{\mu_a^{init}}$$

where $\mu_a^{init} = \mu_a$ from wound on 3rd day after wound surgery (Day 3 was the earliest wound measurement). Similar results were obtained for all wavelengths.

Near Infrared Scattering Data ($\mu_s$)

Figure 5:
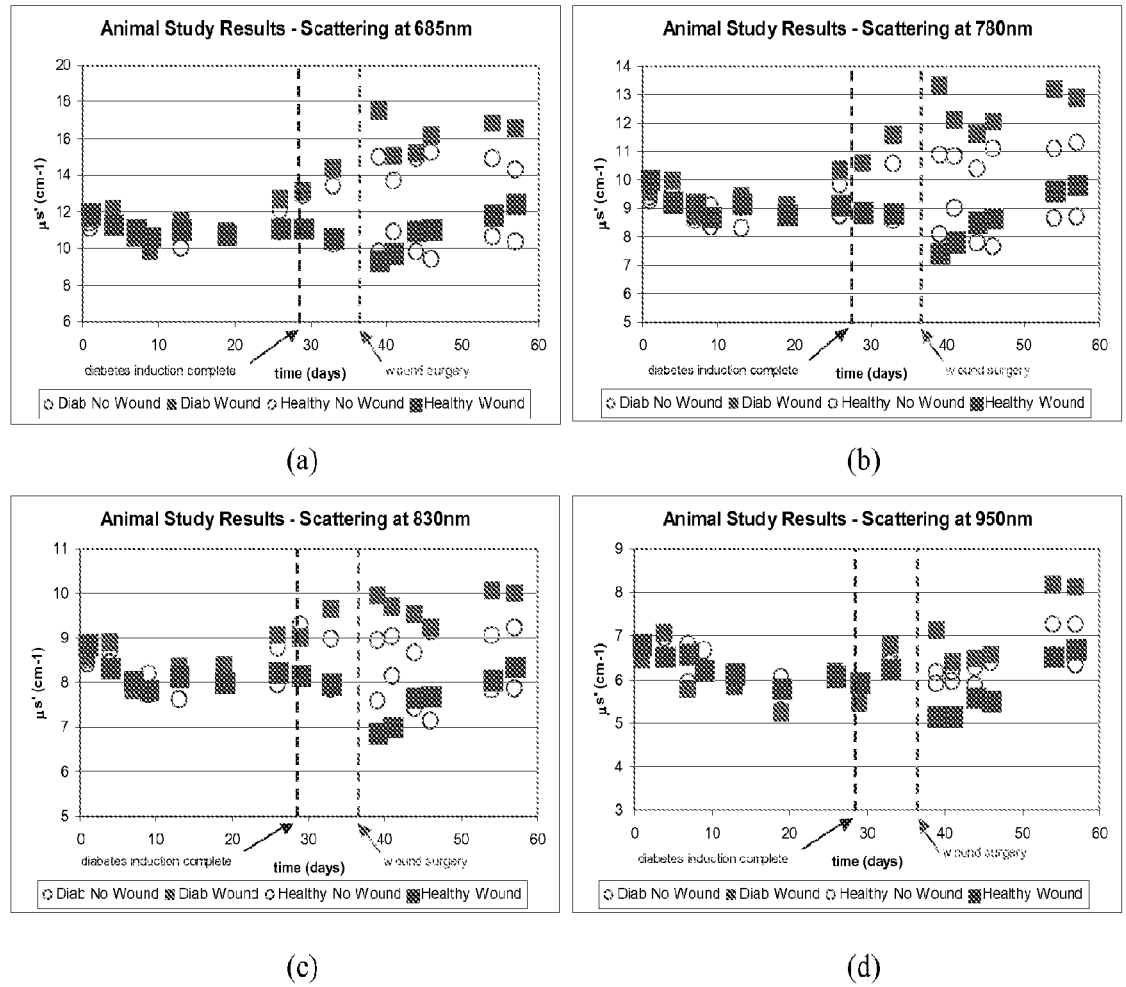
FIG. 5 illustrates the average reduced scattering coefficient ($\mu_s'$) in diabetic non-wound tissue, diabetic wounds, healthy non-wound tissue, and healthy wounds at (a) 685 nm, (b) 780 nm, (c) 830 nm, and (d) 950 nm.

Scattering coefficients also increased in the diabetic rats starting soon after the induction of diabetes. As illustrated in FIG. 5, the average scattering coefficients were significantly higher in the diabetic wounds when compared to the diabetic non-wounded side and to the controls soon after wounding and over the time of healing.

Figure 6:
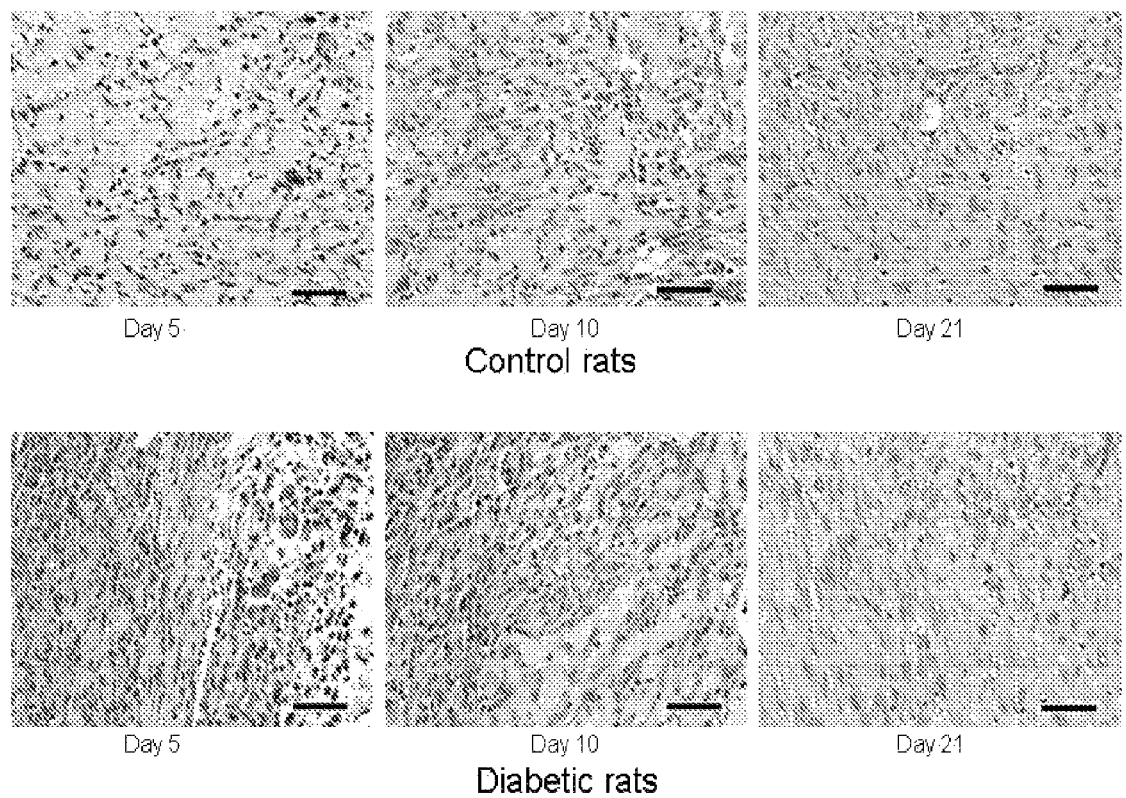
FIG. 6 illustrate the status of wound healing whereby on Day 5 and Day 10 a significantly higher number of neutrophils in the diabetic wounds are present, which was not as apparent on Day 21, although on Day 21 there was more organized tissue in the control wounds.

FIG. 6 illustrate the status of wound healing where on Day 5 and Day 10 a significantly higher number of neutrophils in the diabetic wounds are present. This was not as apparent on Day 21; however, on Day 21 there was more organized tissue in the control wounds. In FIG. 6, a scale bar represents 50 µm.

Figure 7:
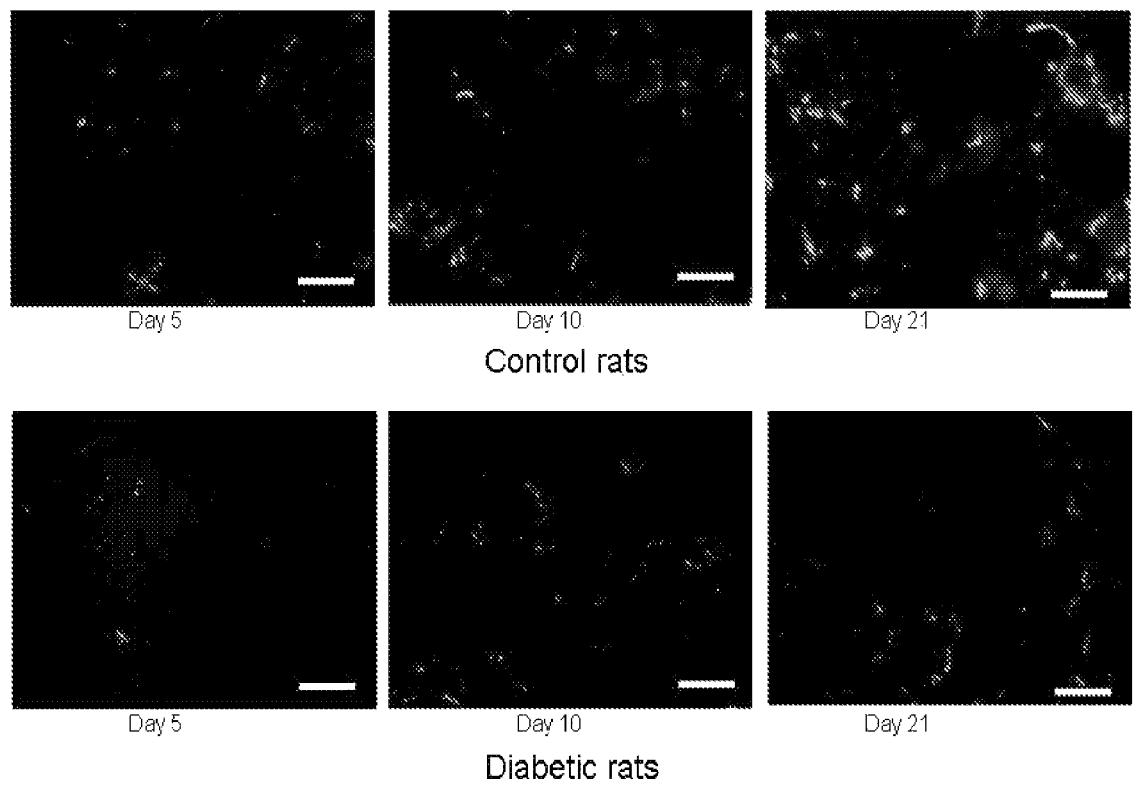
FIG. 7 illustrates lectin staining of the wound demonstrating decreased vascularity in the diabetic wounds compared to the control wounds.

FIG. 7 illustrates using lectin staining that the wound demonstrated decreased vascularity in the diabetic wounds compared to the control wounds. In FIG. 7, a scale bar represents 25 µm.

Figure 8:
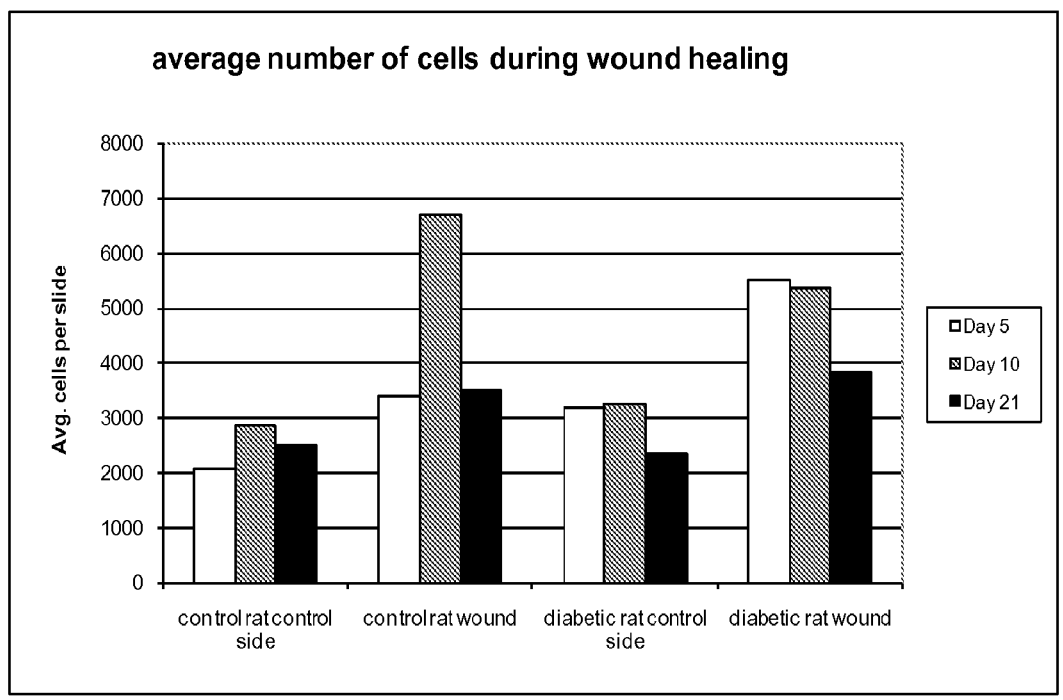
FIG. 8 illustrates image analysis of DAPI-stained tissue samples for a total number of cells per image.

An image analysis of the specimens stained with DAPI found that the control wounds have more cells at Day 10 consistent with the normal wound healing processes; at day 5 cell counts could be mostly dominated by neutrophils, explaining the higher counts seen in the diabetics (FIG. 8). This is consistent with impaired wound healing in this model. There was no statistical correlation between the µs' from NIR and Cell counts from the DAPI image analysis, because scattering is affected both by cells and collagen.

Trichrome Staining for Collagen

Figure 9:
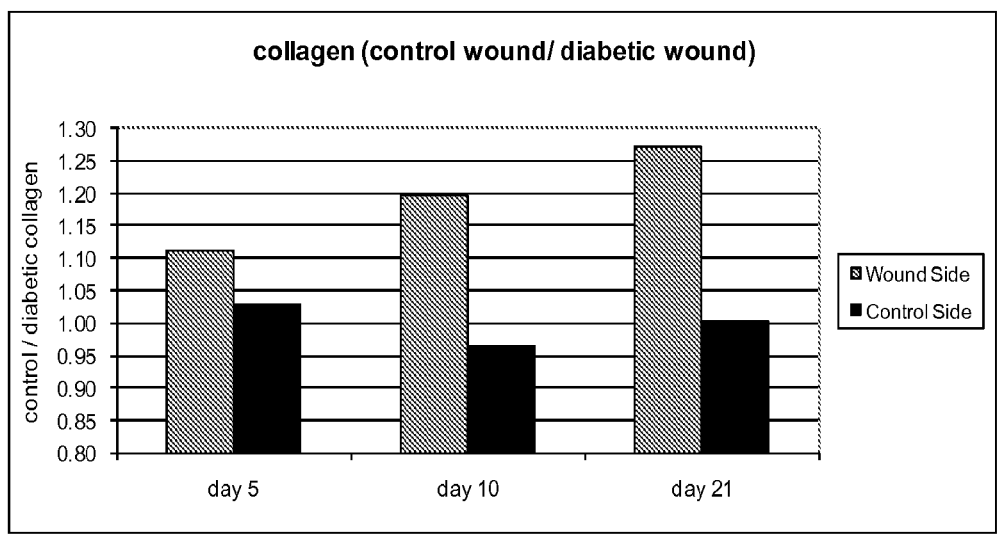
FIG. 9 illustrates the ratio of collagen concentration in a control vs. diabetic wound as determined by image analysis of trichrome stained tissue specimens.

Relative collagen concentration was calculated by image analysis of trichrome stains of tissue. Collagen concentration was decreased in the diabetic wounds when compared to the control wounds over time, as shown in FIG. 9.

DRS Data

Figure 10:
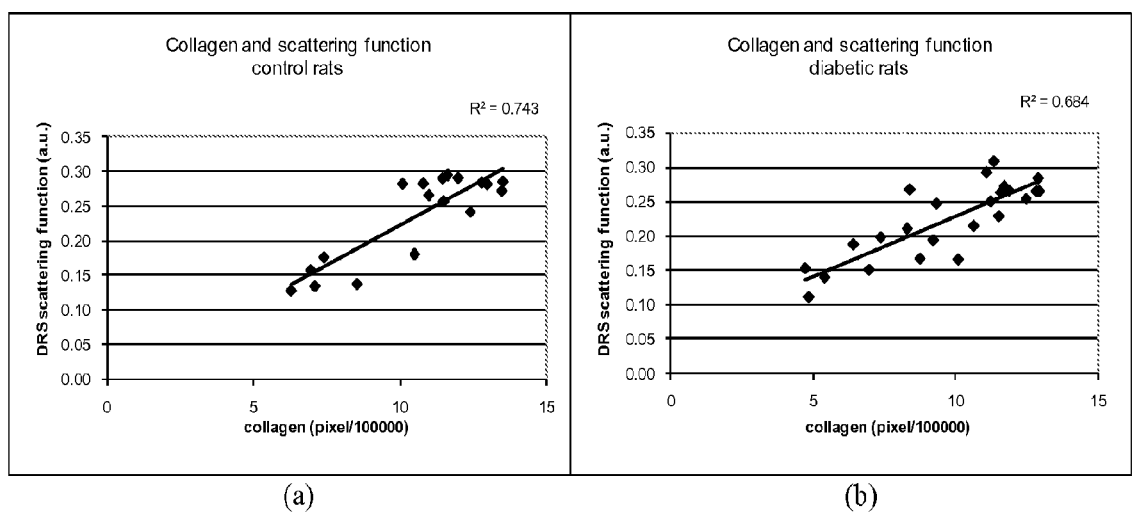
FIG. 10 illustrates a DRS scattering function (arbitrary units) vs. relative collagen concentration as determined by image analysis of trichrome stained tissue specimens, showing a strong correlation between the DRS scattering function and collagen concentration found for both (a) control rats and (b) diabetic rats.
Figure 11:
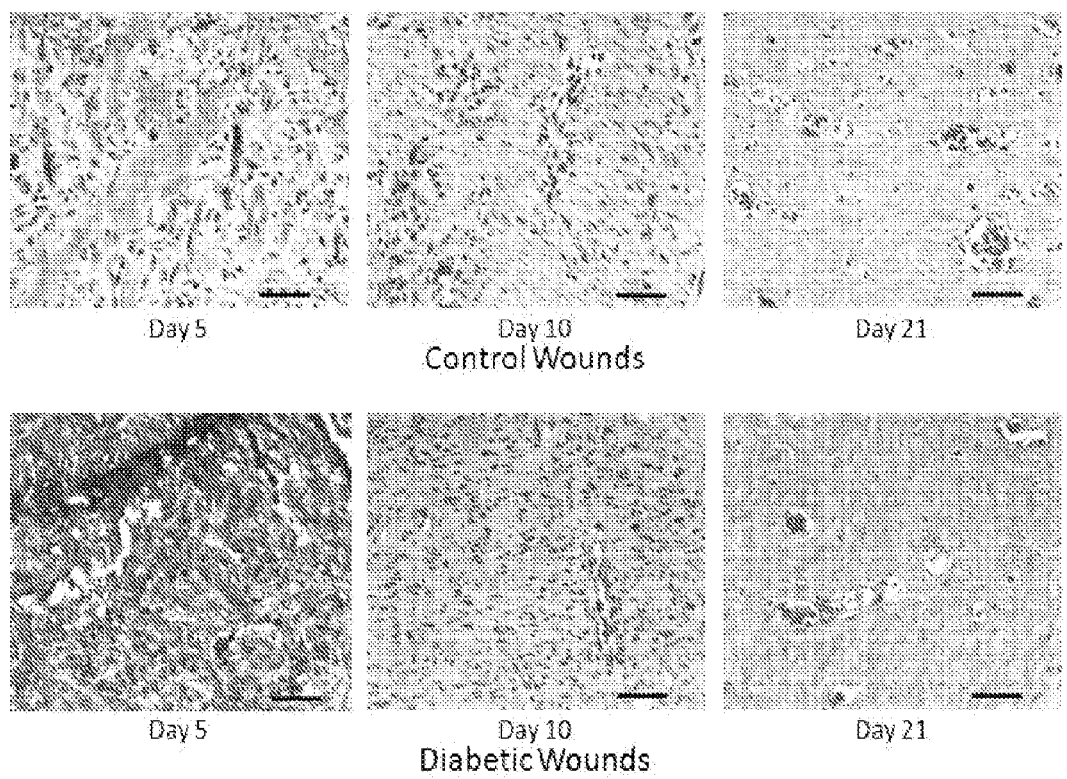
FIG. 11 illustrates trichrome staining for blood vessels.
Figure 12:
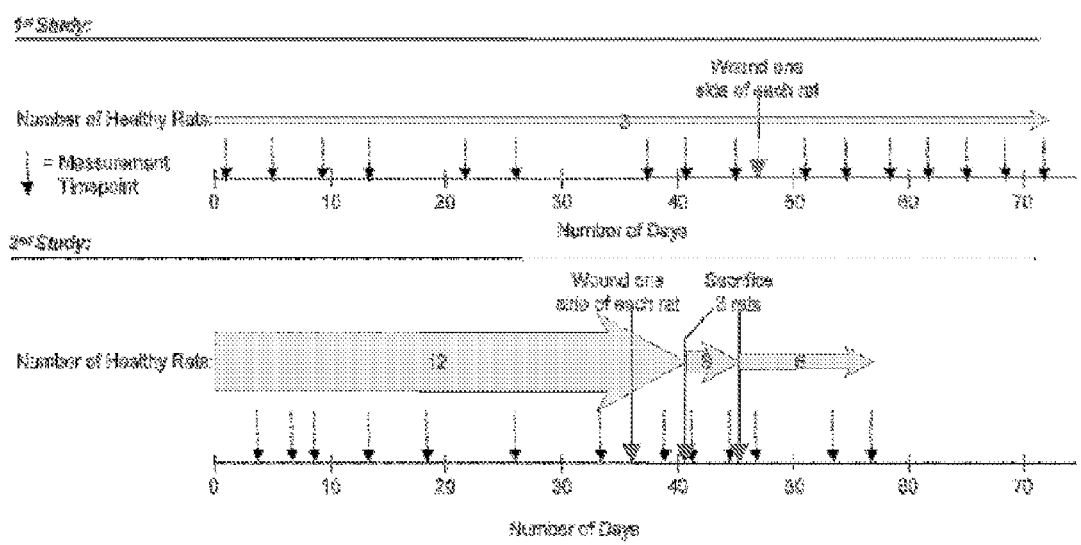
FIG. 12 illustrates a timeline of animal studies performed by the inventors for measuring wound healing.

As illustrated in FIG. 10, collagen correlated with the DRS scattering function. As also illustrated in FIG. 10, the DRS scattering function obtained over time in the diabetic and control wounds also correlated with the increase in collagen observed during healing. As illustrated in FIG. 11, the diabetic wound had lower blood vessel ingrowth as predicted by the absorption coefficient data.

Discussion

The experiments described above demonstrate that near infrared spectroscopy may be used to gather data suitable to differentiate the rate of normal wound healing from impaired (delayed) healing in an animal model. Rising values of absorption coefficients at 685 nm, 785 nm, and 830 nm during normal wound healing suggested that blood volume was increasing as blood vessel ingrowth progressed. There was also a marked difference in scattering coefficients in the diabetic wound, suggesting a connection to the number of inflammatory cells or correlating to a decreased collagen concentration. The scattering coefficient may also be a function of collagen or blood vessel organization. The NIR scattering coefficient in this model does not correlate with collagen concentration or cell count, but it does correlate to vessel organization, possibly due to the depth of tissue probed.

Diffuse Reflectance Spectroscopy (DRS) is a noninvasive optical method that provides quantitative information about the structure and composition of the superficial 500 µm at most of a biological tissue DRS directly measures the attenuation of an optical signal when light of wavelength between 330 and 830 nm is emitted into the tissue. While absorption is primarily due to the chromophores deoxy and oxy-hemoglobin, the scattering properties may be related to the size and distribution of cells, organelles, and heterogeneous tissue structure, and are mainly affected by the collagen fibers of the stroma. Collagen fibers are about 2-3 µm in diameter which is composed of collagen fibrils about 0.3 µm. Scattering from collagen fibers is dominant in the visible range. Near infrared spectroscopy (NIR) uses wavelengths from 700-1000 nm and has a greater penetration depth than DRS depending on the distance between source and detector fibers (3-5 mm for the probe used). DRS can only give information from 100-500 microns. Because of the penetration depth and the wavelength used in DRS, blood vessel organization and presence of neutrophils is less a factor in DRS scattering as compared to collagen concentration. These two methods therefore provide complementary information.

In the above experiments, the inventors were able to determine the difference in the change of the absorption coefficient during the wound healing period. In the control wounds, the rate of change in absorption coefficients (FIG. 4) was consistently higher at 685 nm, 780 nm, and 830 nm compared to the diabetic wounds. This is the behavior predicted by vessel ingrowth in the control as blood vessel growth in the control proceeded more rapidly. This was confirmed by image analysis of the trichrome and lectin stains for vessel density. The scattering function determined by DRS correlated very well with collagen concentration determined by trichrome staining in both the diabetic and control wounds.

In summary, absorption coefficients obtained using near infrared spectroscopy correlated with blood vessel ingrowth seen histologically and by vessel staining during healing and could differentiate the chronic wounds (e.g., diabetic, pressure ulcer, venous ulcer, ubiquitous ulcer, and/or ischemic wounds) from the control (non-impaired or normally healing) wounds and to identify pressure ulcers and/or venous ulcers in the wound. Scattering function data obtained using Diffuse Reflectance Spectroscopy (DRS) correlated with increasing collagen concentration during the healing phase. The use of near infrared imaging of wounds may allow the clinician to assess normal wound healing and develop an optimal wound healing trajectory based on histological correlates. Active wound healing agents such as hyperbaric oxygen and topical growth factors would be expected to shift the healing trajectory of the impaired wound towards that of the normal. The data gathering technique described above may be used to monitor values that may be, in turn, correlated to the healing state of the wound to, for example, enable a researcher to study the healing process and any mechanisms that interfere with the healing process. The healing state of the wound also may be used to determine whether any diagnosis or treatment are necessary.

Deep Tissue Monitoring of Wounds

As noted above, diffuse reflectance spectroscopy (DRS) techniques may be used to collect data regarding wound tissue for depths up to 1 mm. However, by using Diffuse Photon Density Wave (DPDW) methodology of near infrared spectroscopy, one may further investigate tissue physiology from a few millimeters up to several centimeters below the skin or tissue surface. Specialized instruments are built and operated at near infrared wavelengths (650-870 nm) where the tissue appears as transparent as possible to that light. At these wavelengths the absorption coefficient $\mu_a$ of tissue is markedly lower than its value at visible wavelengths. The propagation of light in tissue is characterized by three phenomena: scattering, absorption and reflection from various layers. The diffusion equation can describe light propagation in tissue if the characteristic distance between successive photon scattering events (mean free path) is much less than $1/\mu_a$ but larger than the wavelength of incident light. Then the dominant phenomenon of light propagation in tissue is multiple light scattering by cells, organelles, capillaries, and other interfaces and tissue structures. This is indeed the case at NIR wavelengths, where absorption of hemoglobin, water and lipids is relatively very small (for hemoglobin less by a factor of 30-50 compared to absorption at 540-580 nm, the range used in DRS methodologies for determining blood oxygenation). Furthermore, at a selected range of NIR wavelengths, the spectra of oxy and deoxy hemoglobin are significantly different from each other and allow calculation of absolute concentrations of both types of hemoglobin, and consequently, oxygen saturation, if their extinction coefficients at the particular wavelengths are known. For special boundary conditions of the diffusion equation, simple closed form solutions can be obtained that allow calculation of absorption and scattering coefficients at specific NIR wavelengths from experimental data.

The DPDW method can yield quantitative information about blood oxygenation and blood volume, water and lipid content, as well as qualitative information about changes of tissue structure. There are many biomedical applications where use of this non invasive optical method be used to gather data that is, in turn, used by physicians to diagnose a wide range of medical pathologies. This includes cases where blood supply to the tissue changes significantly as a result of the disease, as in tumor angiogenesis. In stroke, aneurysm, or brain damage and head injury bleeding or ischemia can be determined by optical methods. Additional applications lie in the areas of hemodynamics of human muscle, peripheral vascular diseases, control of photodynamic therapy (PDT) and monitoring of lesions.

The potential of using the DPDW methodology to characterize subcutaneous lesions and assess the necrotization depth of burns was discussed for the first time in a paper by Tromberg et al. entitled "Reflectance measurements of layered media with diffuse photon-density waves: a potential tool for evaluating deep burns and subcutaneous lesions," Phys. Med. Biol., 1999, Vol. 44(3), pp. 801-813. In a previous study by the present inventors (Papazoglou et al., "Optical Properties of Wounds: Diabetic Versus Healthy Tissue," IEEE Transactions on Biomedical Engineering, 2006, Vol. 53(6), pp. 1047-1055), the use of DPDW methodology at NIR wavelengths to distinguish the optical properties of diabetic wounds from normal wounds in an animal model was reported. In that study, the results of two new animal studies in which temporal changes in the optical properties of wound and non-wound tissue are monitored with DPDW methodology at NIR wavelengths throughout the course of wound healing were reported. The absorption and scattering coefficients can be calculated, and blood oxygenation can be quantified by using the diffusion approximation with the semi-infinite boundary condition. The inventors' approach has been to measure optical properties of the wound tissue in vivo and to calculate tissue oxygenation using the optical absorption coefficient. Since depth penetration is accomplished at relevant physiological depths, there is no need for empirical fitting of spectroscopic data. The data obtained from in vivo measurements taken in accordance with the invention strengthen and support the conclusions of Tromberg et al on the advantages of using DPDW to study necrotic burn tissue or skin lesions. Differences in tissue optical properties between the wound and non-wounded site during the course of healing can reveal information about physiological changes of the tissue, such as its inflammatory state and its rate of healing. The results presented below indicate that this NIR method would be highly useful in collecting data whose values may be used to monitor and quantify the wound healing process.

Materials and Methods

Optical Methods

A frequency domain DPDW instrument illuminated the animal tissue with four diode lasers in the near infrared window at wavelengths of 685, 780, 830 and 950 nm, with its intensity modulated by a radio frequency $\omega=70$ MHz. A schematic of the device and a detailed description can be found in the afore-mentioned article by Papazoglou et al. entitled "Optical Properties of Wounds: Diabetic Versus Healthy Tissue," IEEE Transactions on Biomedical Engineering, 2006, Vol. 53(6), pp. 1047-1055. Backscattered light was delivered to four detector blocks based on Avalanche Photodiodes (APD) and quadrature (I/Q) demodulators. The I and Q signals in each detector were measured, and these were determined by the attenuated amplitude $A_{att}$ and phase shift $\Theta_{lag}$ of the registered scattered light. The output power at the end of the source fiber ranged from 5 to 7 mW, for all four wavelengths.

The diffusion approximation can be used to calculate absorption $\mu_a$ and reduced scattering $\mu'_s$ coefficients of tissue based on the solution of the time-dependent diffusion equation assuming a semi-infinite tissue geometry as described by Haskell et al. in "Boundary conditions for the diffusion equation in radiative transfer," J. Opt. Soc. Am. A, 1994, Vol. 11(10), pp. 2727-2741, and by Pham et al. in "Broad bandwidth frequency domain instrument for quantitative tissue optical spectroscopy," Review of Scientific Instruments, 2000, Vol. 71, pp. 2500-2513. The closed form analytical solutions to the diffusion equation were used for calculating the optical properties of animal tissue using the techniques disclosed by Pham et al. The so-called extrapolated condition for semi-infinite media was found to be a good approximation in non-invasive clinical applications where the fluence rate is nonzero at the boundary.

During this diffusion and "snake-like" propagation of light in the tissue, light is attenuated in intensity and also subjected to a phase shift which reflects the mean flight time of photons through the strongly scattering medium (tissue). The reduced scattering coefficient is defined as a function of the scattering coefficient $\mu_s$, $\mu'_s=\mu_s(1-g)$, where the average cosine angle of scattering $g\sim0.9$ for biological tissue and its inverse is defined as the mean transport length $l^*$. Usually after propagation of more than two or three $l^*$, photons have no memory of the incident direction of light and it can be assumed that the radiance is quasi-isotropic.

For most biological tissues $\mu'_s$ is between 5-15 cm$^{-1}$ and its value determines the design of the appropriate experimental probe. In studies conducted by the present inventors, it was assumed that $\mu'_s\sim10$ cm$^{-1}$ for animal tissue and an optimal probe was designed. The scattering coefficient calculated from the present studies was very close to the assumed value of 10 cm$^{-1}$, corresponding to $l^*$ around 1 mm. Since the smallest source detector separation of the probe (4 mm) used by the inventors is larger than $3^*l^*$, the diffusion approximation will be valid.

The optical fibers were inserted in a Teflon probe of length 25 mm and width 7 mm, with a separation between source and detector fibers of $\rho=4$, 8, 12 and 16 mm. It is possible to estimate the probable penetration depth of diffuse light $D_v$ in the tissue as function of the source-detector separation $\rho$ by using diffusion theory. A detailed investigation of this problem can be found in articles by Fridolin et al. entitled "Optical non-invasive technique for vessel imaging: II. A simplified photon diffusion analysis," Phys. Med. Biol., 2000, Vol. 45(12), pp. 3779-92, and by Weiss et al. entitled "Statistics of Penetration Depth of Photons Re-emitted from Irradiated Tissue," Journal of Modern Optics, 1989, Vol. 36(3), pp. 349-359, but a rule of thumb often applied is that: $D_v\sim(1/3-1/2)\rho$.

Calibration Procedures

The measured intensity of scattered light $A_{att}$ depends not only on the tissue properties, but also on the sensitivity of the Avalanche Photodiode (APD), the coupling to the detectors fibers, the transmission of the optical fibers and the gain of each detector block. The phase shift $\Theta_{lag}$ may be different in each channel because the optical and electrical signal delay depends on fiber length and coupling, the length of the RF coaxial cables, and any delays in the detector circuits. Instrument calibration is performed to allow separation of the variability due to the instrument hardware components from sample and measurement variability.

An equidistant probe is constructed to conduct the first instrument calibration. The four detector fibers are inserted in a Teflon probe with the same source-detector separation of 12 mm. The probe is placed on the surface of a liquid optical phantom (Intralipid) that simulates tissue optical properties in a semi-infinite geometry. The set of calibration coefficients that equalizes the amplitude and phase of the $2^{nd}$, $3^{rd}$ and $4^{th}$ detector relative to the $1^{st}$ detector is determined. All subsequent experimental data are corrected using this set of calibration coefficients.

It should be noted that the use of an Intralipid solution as an optical phantom for experiments that span several days is not the best approach, because the solution changes optical properties due to phase separation and degradation. An additional factor that contributes to operator variability when using Intralipid is the repeatability of placing the solid plastic probe exactly on the surface of the solution. Use of the semi-infinite approximation relies on perfect contact between the solid and liquid interface, without any air gap and also without immersing the probe in the liquid. Solid phantoms can overcome some of these challenges. Silicone optical phantoms were the method of choice for calibrating the NIR device because these models do not change optical properties during the time course of our experiments. Cylindrical phantoms made of silicone with dispersed particles of titanium dioxide to act as scatters and carbon black to act as an absorber were used. Cylinders with diameter of 90 mm and thickness of 45 mm were synthesized from silicone XP565 with activator (platinum catalyzed from Silicones Inc), and $TiO_2$ particles with diameter between 0.9-1.6 μm simulated tissue scattering and carbon black acetylene, 50% compressed, 99.9+% (metals basis) (diameter=0.042 μm) simulated light absorption. Both $TiO_2$ and carbon black were obtained from Alfa Aesar.

The inventors optimized the preparation of these models including intensity and time of mixing, the order of addition of the components and the crosslinking reaction to ensure phantoms of desired composition with no air bubbles. The absence of microbubbles was verified by sectioning the phantoms in thin layers and observing their surfaces under an optical microscope.

Typical of any device that measures light intensity, the instrument has a limited range where the electrical output signal is proportional to the optical power of the input signal. A second calibration was thus conducted to define the region of saturation which occurs at an output signal of around 100 mV. The linearity range for the device used in this study was >50 dB. Typical magnitudes of the I and Q demodulation signals were in the range of 2-70 mV. Offset for the instrument, defined as the signal measured without any light, was measured before every experiment on an animal and has not exceeded 500 μV for any experiment, with an average value around 250 μV throughout the studies. This calibration experiment allows one also to calculate the Noise-Equivalent Power (NEP) for the device, which was equal to 5 pW/Hz.

Animal Models

Hairless rats were used as the animal model for studying tissue optical properties during wound healing. This is a model that is widely used and accepted for studying skin and wound properties. The absence of hair removes the complications of inflammation introduced by shaving the wound site, and does not interfere with the optical measurements.

Figure 13:
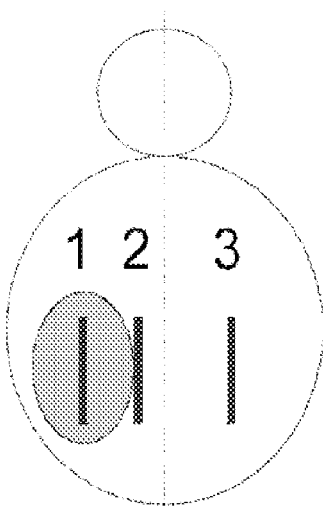
FIG. 13 illustrates the probe placement locations (dark rectangles) in an animal model, where each animal was wounded on the left dorsum and measurements were performed on (1) the center of the wound, (2) the edge of the wound, and (3) healthy tissue on the right dorsum, symmetric to the wound location.

Two independent studies were performed as described below:

$1^{st}$ STUDY: Three female hairless Sprague Dawley rats, 5-6 weeks old and approximately 150 g each, were purchased from Charles River Laboratory (Wilmington, Mass.). A measurement protocol was developed over the course of 15 weeks, and when measurements began the rats weighted approximately 300 g each. The rats were monitored with NIR for 48 days (FIG. 12), with independent measurements taken usually every 3-4 days. On the 48th day, one quarter-sized (4.6 $cm^2$) full thickness wound (FIG. 13) was inflicted on the left dorsal area of each animal in order to produce a wound animal model on all rats. A full thickness wound is a superficial wound where the epidermis and dermis are removed to expose the underlying tissue. It is different from an incision wound and it heals by contraction. Sixteen series of optical measurements were performed on the wound and on skin bordering the edge of the wound. Symmetrical measurements were performed on the right dorsal side of all animals (FIG. 13).

$2^{nd}$ STUDY: Twelve healthy rats identical to the ones in the first study were purchased and allowed to acclimate to their surrounding for 4 weeks until they weighed approximately 200 g each. Baseline near infrared data were collected on all rats for 33 days (FIG. 12), with independent measurements taken every 3-4 days. On day 36 a full thickness wound 4.6 $cm^2$ was made using sterile technique in an animal surgical suite. One wound was inflicted on the left side of the dorsal area of each animal. The right side of each animal was left unwounded to provide a control site. NIR measurements were performed on the wounds and control sites until day 57 (FIG. 13) when the wounds were completely re-epithelialized. The wound surgery and all optical measurements were performed using isoflurane and oxygen anesthesia administered via face mask to prevent the animals from moving. It was necessary to anesthetize the animals to eliminate motion artifacts before performing NIR measurements. Animals were measured as soon as they stopped moving and NIR measurements lasted 5 minutes at most. All wounds were covered with a Tegaderm (3M, Minneapolis, Minn.) sterile transparent dressing after wound surgery and between optical measurements. After surgery all rats were fitted with "Elizabethan" type collars to prevent them from scratching their wounds.

Immunohistochemistry

Tissue Excision

During the second study, three rats were sacrificed by $CO_2$ suffocation on days 5 and 10 after wound surgery, respectively. The wound and surrounding skin were completely excised, as was the area of the dorsum contralateral to the wound. This procedure was repeated for the remaining 6 rats on day 21 after wound surgery. All excised tissue was immediately frozen at −80° C. until needed.

Blood Vessel Staining

Lectin staining (a sugar binding protein of non-immune origin that agglutinates cells or precipitates glycoconjugates) was used to stain vessels in the tissue, and visualize vascularization. Lectin can be used as a marker of angiogenesis because it binds to endothelial cells and reveals the overall vascular architecture. Briefly, sections were washed in 1×PBS for 10 minutes after rehydration. Sections were stained with Alexa Fluor 488 conjugated lectin (Invitrogen L2-1415) for 30 minutes in the dark with a concentration at 1:250 and washed with 1×PBS 3 times for 5 minutes each.

Results

Baseline

Figure 14:
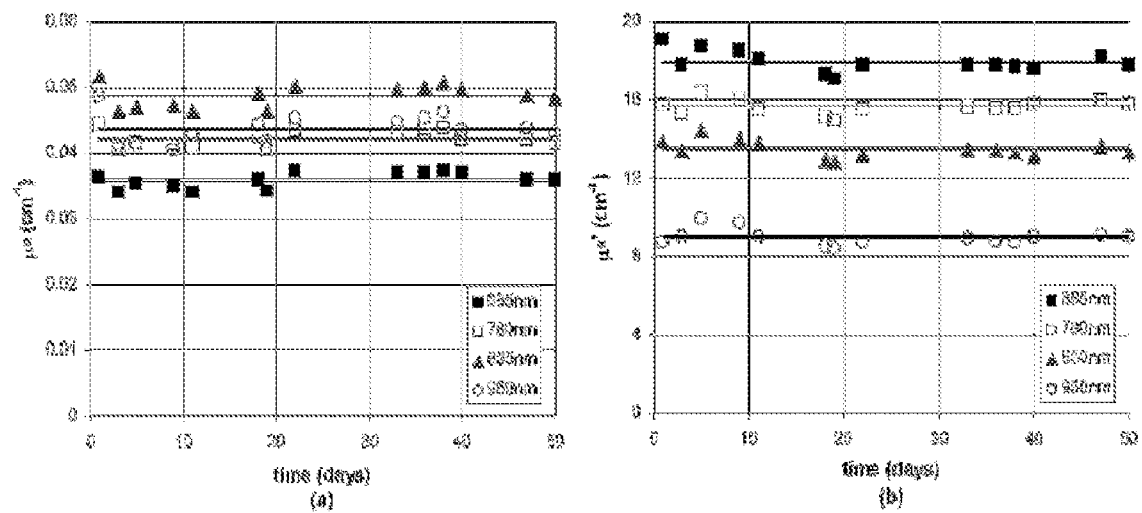
FIG. 14 illustrates the daily average values of (a) $\mu_a$ and (b) $\mu_s'$ in a silicone optical phantom over a 50-day period where each point represents the average of measurements taken on the same day and solid lines represent average values for the entire measurement period.

The stability and accuracy of the frequency domain NIR instrument used in the study is demonstrated in FIG. 14, which tracks the absorption and reduced scattering coefficients over the course of 50 days measured in silicone phantoms. Standard error remained at less than 4% throughout the period of the study. Of course, those skilled in the art will appreciate that appropriate time domain NIR instruments may be used as well.

In order to be able to detect the small changes in optical properties occurring during wound healing the NIR device used should exhibit very good stability. Otherwise it would be impossible to discern systematic device drift from actual physiological changes. The 48-day and 36-day periods of in vivo measurements prior to wound surgery in the $1^{st}$ and $2^{nd}$ studies, respectively, allowed the inventors to determine with high consistency the local values of $\mu_a$ and $\mu'_s$ for the animals.

Figure 15:
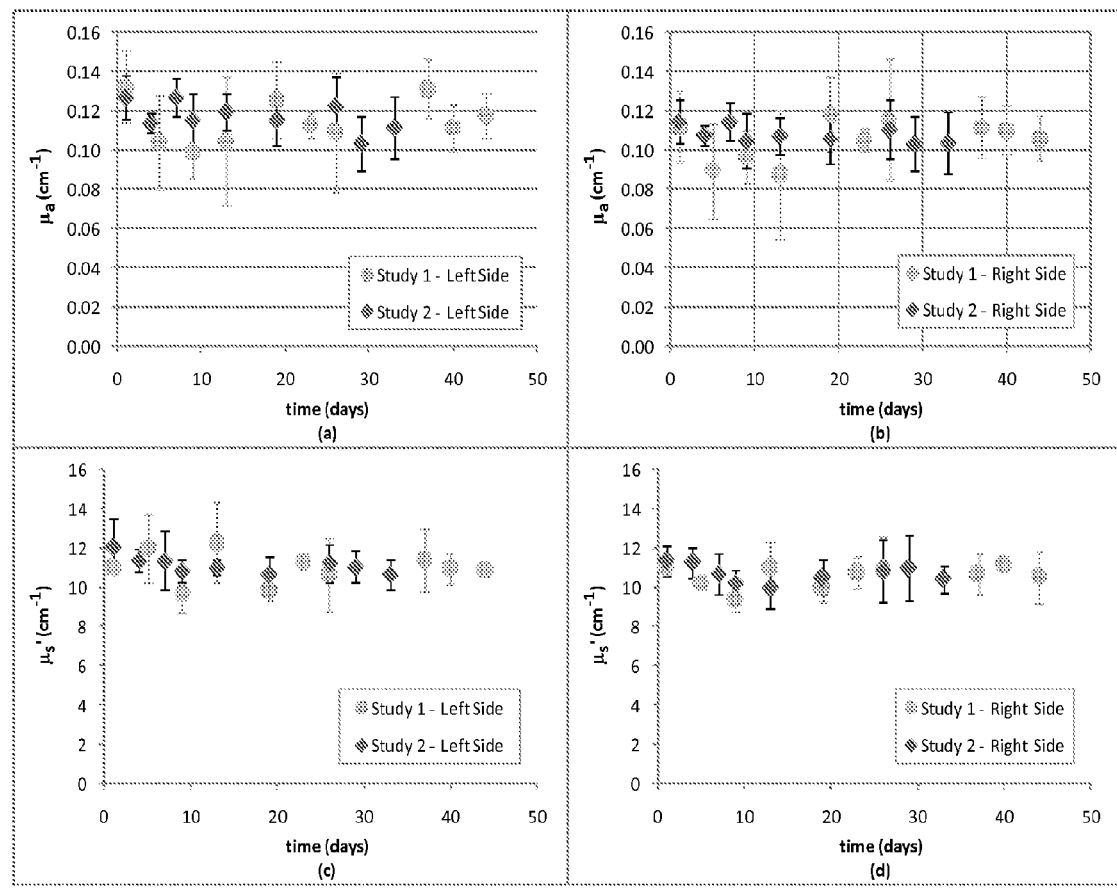
FIG. 15 illustrates the average absorption and scattering coefficients for all animals measured as a function of time, including baseline values of (a) left dorsal $\mu_a$, (b) right dorsal $\mu_a$, (c) left dorsal $\mu_s'$, and (d) right dorsal $\mu_s'$ at 685 nm from study 1 and study 2.

These values form the baseline measurements for assessing changes in optical properties during the wound healing studies. Combined results of baseline measurements for $\mu_a$ and $\mu'_s$ from both animal studies are shown in FIG. 15 for 685 nm. The error bars in FIG. 15 indicate the between-animal variation, which was less than 15% percent of the average values of $\mu_a$ and $\mu'_s$ for each time point in study 2. Similar results were obtained for 785 nm and 830 nm measurements. Baseline measurements for three representative rats are presented in FIG. 16. Within-animal variation was less than 15% of the average values of $\mu_a$ and $\mu'_s$ for each animal in the second study.

It is noted that FIG. 15 illustrates the average absorption and scattering coefficients for all animals measured as a function of time. Baseline values of (a) left dorsal, (b) right dorsal, (c) left dorsal, and (d) right dorsal at 685 nm from study 1 and study 2 are illustrated. Each point represents the average of measurements taken on that day; error bars represent the standard deviation. In both studies, baseline optical measurements were taken at symmetric locations on the left and right dorsa of each animal. The average data of baseline stability obtained during the 2nd study (black points) is a better indicator of device stability because of the higher number of animals (n=12) compared to n=3 in the first study (gray points).

Figure 16:
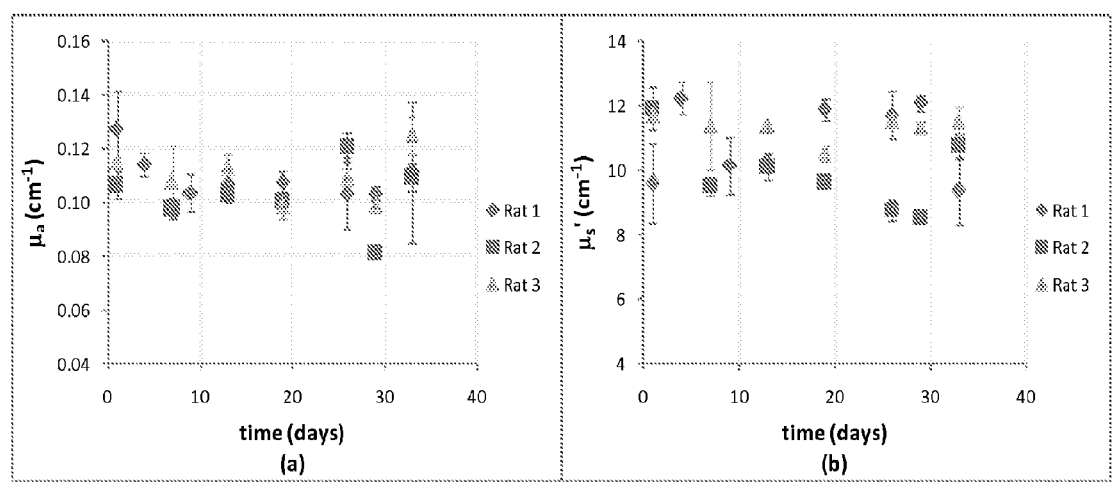
FIG. 16 illustrates left dorsal baseline values of (a) $\mu_a$ and (b) $\mu_s'$ from three representative rats where each point represents the average of three measurements and error bars represent the standard deviation.
Figure 17:
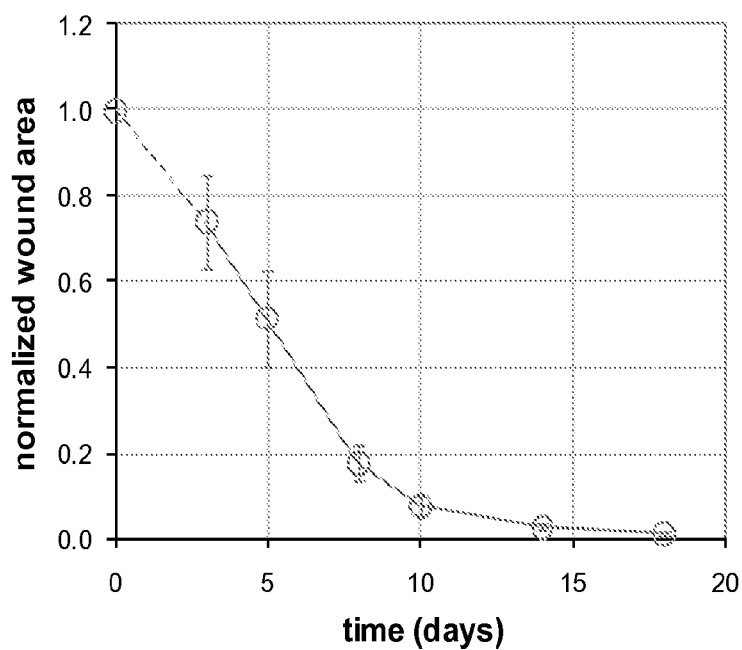
FIG. 17 illustrates a normalized wound area as a function of healing time for rats in study 2 where each point represents the average of all rats (n=12) and error bars represent the standard deviation.

FIG. 16 illustrates left dorsal baseline values of (a) and (b) from three representative rats. Each point represents the average of three measurements and error bars represent the standard deviation.

If the in vivo data is compared with those obtained from phantoms, it is clear that in addition to the noise from the laser-diodes, electronics, and fibers, being common to both in vitro and in vivo measurements, additional noise emanates from physiological changes in the animal tissue during the experiments. Several reasons may be responsible for such changes: The size of the rat is small, even compared to a 2 cm probe. The rats were anesthetized during measurements and unable to move; however breathing may have contributed to unintended change in probe positioning. The food supply was provided ad libitum, and this may have affected the amount of blood at the measurement sites at various times. Rats have been growing during the period of baseline measurements and therefore a slightly different tissue volume was examined as time went on.

Attention is drawn to the fact that absorption coefficient is systematically higher for the left dorsal side as compared to the right one, for all animals at all timepoints (FIG. 15). During the 2nd study the differences between the two sides range from 0.01-0.015 cm and this may be due to asymmetry in the animal physiology.

Optical Properties During Wound Healing

In the experiments, wound size was determined by calculating wound surface area from cross-polarized digital images, taken at the same time the near infrared data was collected. The image analysis tool IMAGE PRO (Media Cybernetics, Silver Spring, Md.) was used to calculate the area of each wound. Although the original size of each wound was large relative to the size of the rat, the wound healing rate was very fast for this model (as with all healthy animals) and evident of the intense physiological changes in the animal during healing. A normalized wound area was obtained by calculating the ratio of wound area each day to the initial wound area on the day of surgery (day 0). Average normalized wound areas are presented in FIG. 17 (Study 2). Wound healing rate in this animal model exhibits a non-linear behavior as reported by Mast et al in "Optical Measurements of tissue oxygen saturation in lower limb wound healing," Adv. Exp. Med. Biol., 2003, Vol. 540, pp. 265-9. From the data, it can be observed that the healing rate is fast between days 3-10 and then decelerates to achieve full wound closure. (Note that the data points on days 0 and 3 are connected by a dashed line because from Mast et al. it is known that the rate exhibits highly non-linear behavior prior to day 3.

Figure 18:
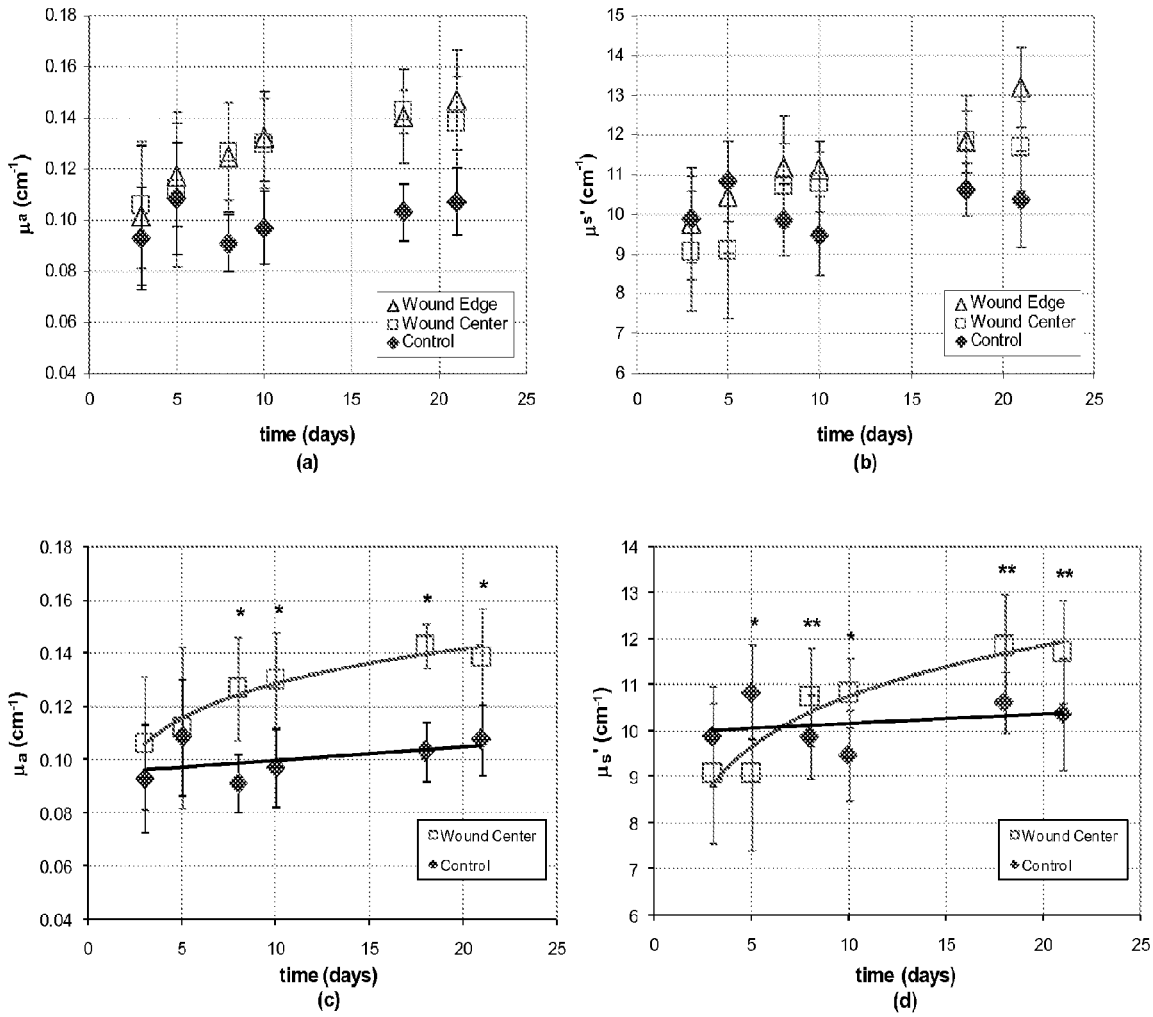
FIG. 18 illustrates (a) $\mu_a$ and (b) $\mu_s'$ at 685 nm during wound healing (average ±standard deviation) for animals in study 1 and (c) $\mu_a$ and (d) $\mu_s'$ at 685 nm during wound healing (average ±standard deviation) for animals in study 2.

The change of optical properties was monitored during wound healing for all animals. Changes of optical properties at 685 nm as a result of the experiments are shown in FIG. 18. The absorption coefficient of the wound is increasing during wound healing and asymptotically approaches a value that is higher by 0.035-0.040 $cm^{-1}$, or 35-40%, (FIG. 18, open squares and triangles) compared to the non-wounded site (FIG. 18, filled diamonds) throughout the experiment. The difference in $\mu_a$ between wound and non-wound tissue is statistically significant ($p<0.01$) after day 5. The difference in $\mu'_s$ between wound and non-wound tissue is statistically significant ($p<0.05$) after day 3. Similarly shaped healing curves were observed at other wavelengths, with $\mu_a$ at 780 nm increasing by 0.030-0.035 $cm^{-1}$ (approximately 35%) and $\mu_a$ at 830 nm increasing by 0.040-0.045 $cm^{-1}$ (approximately 40%) when compared to the non-wounded site.

In FIG. 18, (a) illustrates $\mu_a$ and (b) $\mu'_s$ at 685 nm during wound healing (average ±standard deviation) for animals in study 1. Wound surgery was performed on day 0. Open triangles represent measurements taken on the edges of the wounds; open squares represent measurements taken at the center of the wounds, and closed diamonds represent control measurements on the non-wounded site. In FIG. 18, (c) $\mu_a$ and (d) $\mu'_s$ at 685 nm during wound healing (average ±standard deviation) for animals in study 2. Again, wound surgery was performed on day 0. Open squares represent measurements taken at the center of the wounds, and closed diamonds represent control measurements on the non-wounded site. Two-tailed paired t-tests were performed to compare wound center and control data at each time point (*$p<0.01$, **$p<0.05$).

Figure 19:
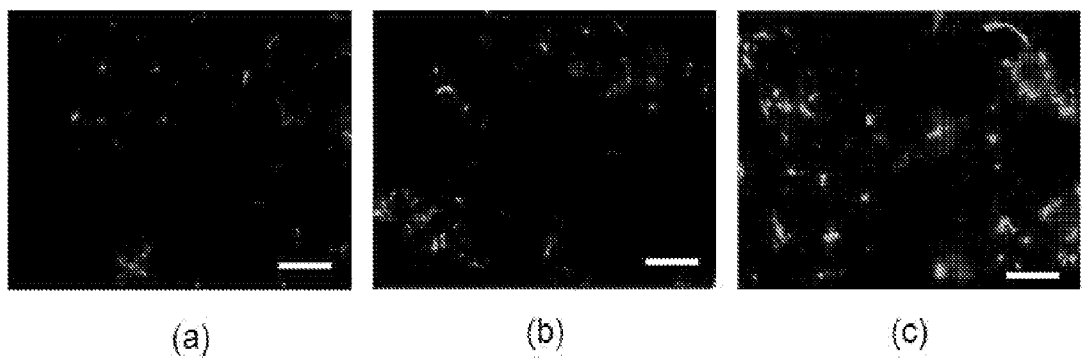
FIG. 19 illustrates lectin-stained images of wound tissue on (a) day 5, (b) day 10, and (c) day 21 after wound surgery.

Increasing values of $\mu_a$ as the wound is healing could be due to angiogenesis and neovascularization and this was supported by immunohistochemical analysis where vessel ingrowth increased with time in lectin-stained images of blood vessels as shown in FIG. 19 for stained endothelial cells. FIG. 19 illustrates lectin-stained images of wound tissue on (a) day 5, (b) day 10, and (c) day 21 after wound surgery where the vascular structures are stained. The number and size of vascular structures increases as the wound heals.

As may be seen from FIG. 18, the values of $\mu_a$ obtained from measurements on the center of the wounds are identical (within experimental error) to the absorption coefficients obtained from measurements of the peri-wound area particularly for the first several measurements when the wounds are large in size compared to the probe. This remained consistent in both animal studies, and can be explained by the geometry of the experiments. Studies of photon penetration depth at these wavelengths with geometry similar to the one used have shown that a probe having a source-detector separation of 16 mm registers scattered light from a tissue volume up to 5 mm beneath its surface (Weiss et al., Statistics of Penetration Depth of Photons Re-emitted from Irradiated Tissue," Journal of Modern Optics, 1989, Vol. 36(3), pp. 349-359. The similarity between optical properties measured at the wound center and wound periphery provides evidence that the measured tissue is located beneath the skin's surface, and therefore overlapping tissue volumes are interrogated as the probe is positioned on the center or the periphery of the wound. This observation may have clinical utility because it indicates that a wound could be monitored without the fiber optic probe touching directly the surface of an open wound.

Figure 20:
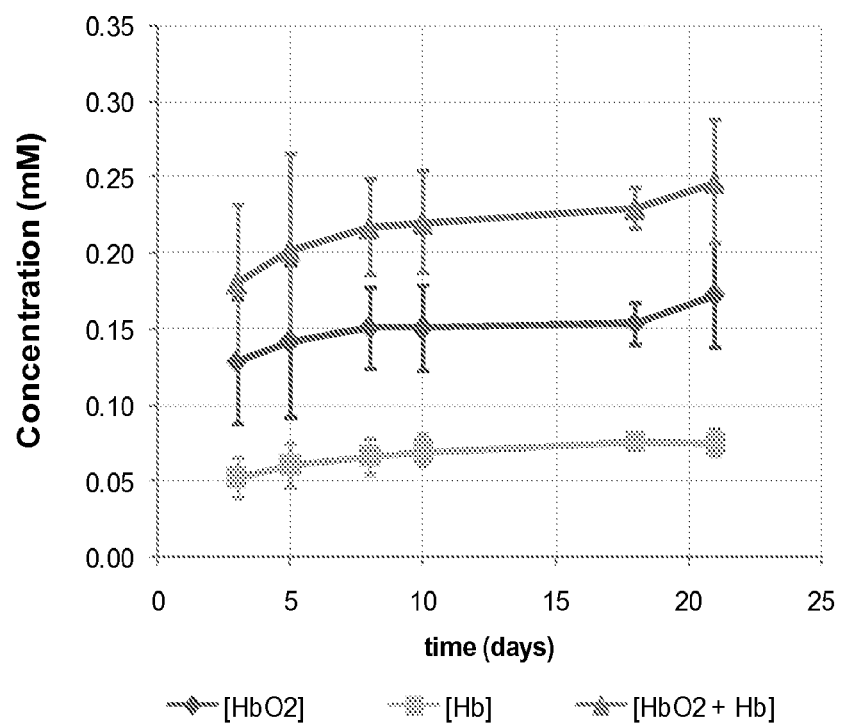
FIG. 20 illustrates mean±standard deviation of oxyhemoglobin [$HbO_2$], deoxyhemoglobin [Hb], and total hemoglobin [$HbO_2$+Hb] during wound healing for animals in study 2.
Figure 21:
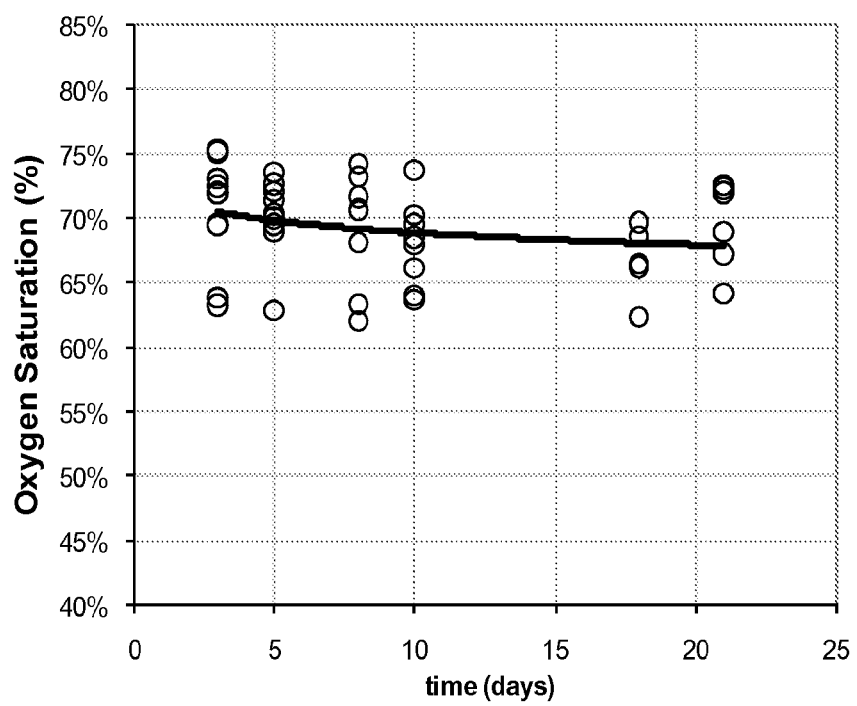
FIG. 21 illustrates oxygen saturation during wound healing for animals in study 2.
Figure 22:
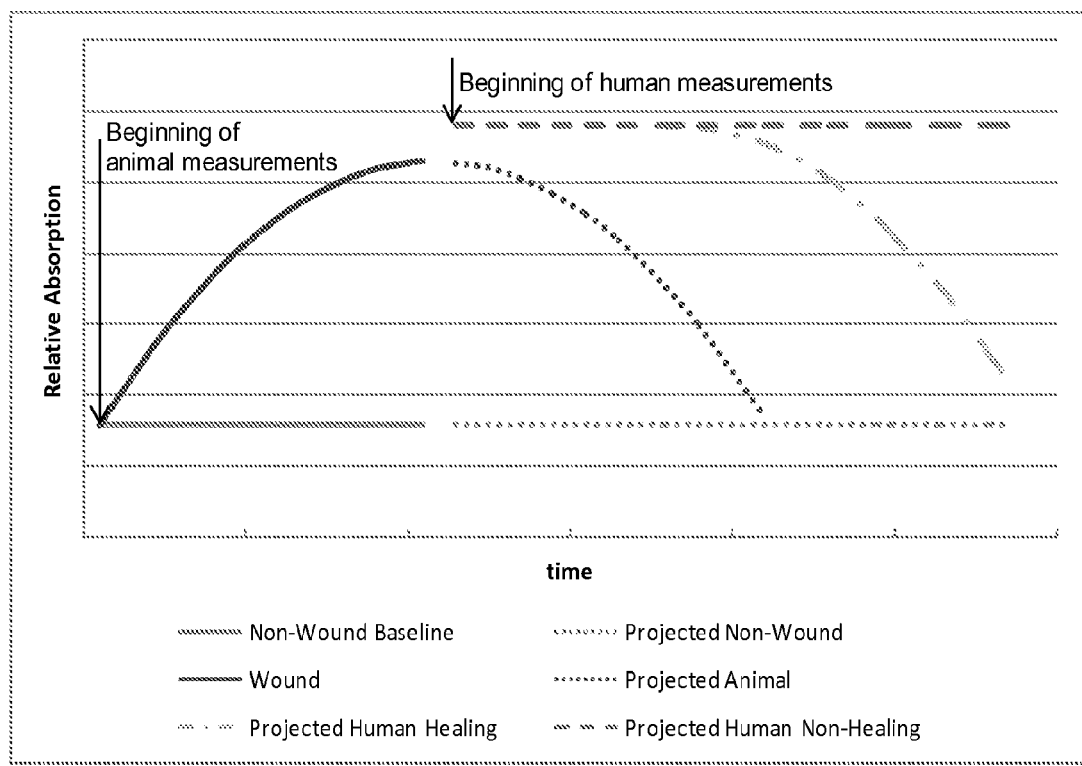
FIG. 22 illustrates a hypothesized clinical wound healing curve compared against the result of the animal study shown in FIG. 18.

The data of FIG. 18 suggest that during normal wound healing the optical properties of tissue at NIR wavelengths change measurably, and therefore healing may be followed by measuring changes of the absorption coefficient of the wound. Oxyhemoglobin concentration ([HbO$_2$]) and deoxyhemoglobin concentration ([Hb]) were calculated from the values of $\mu_a$ and $\mu'_s$ using a modified form of the Beer-Lambert equation:

$$\epsilon_{Hb}^{\lambda}[Hb]+\epsilon_{HBO2}^{\lambda}[HbO_2]+\mu_{a,H2O}^{\lambda}[\% H_2O]= \mu_{a,measured}^{\lambda} \quad (1)$$

where $\epsilon_{Hb}^{\lambda}$ and $\epsilon_{HBO2}^{\lambda}$ are the molar extinction coefficients of deoxy- and oxyhemoglobin, $\mu_{a,H2O}^{\lambda}$ is the absorption coefficient of pure water, and [% H2O] is the percentage of water in the measured tissue, which is assumed to be 70%. Mean hemoglobin values increased during wound healing, as shown in FIG. 20. Within the accuracy limits of the experiment, no significant change in oxygen saturation was obtained during the course of wound healing, as shown in FIG. 21. Oxygen saturation is defined as, $$SO_2 = \frac{[HbO_2]}{[HbO_2 + Hb]},$$

where HbO$_2$ and Hb are the concentrations of oxygenated and deoxygenated hemoglobin.

This small change supports the findings by T. K. Hunt et al. in "Oxygen and wound healing," Hyperbaric Medicine 2000, 8$^{th}$ Annual Advanced Symposium, 2000, and Jonsson et al. in "Tissue oxygenation, anemia, and perfusion in relation to wound healing in surgical patients, Ann. Surg, 1991, Vol. 214(5), pp. 605-613, who suggested that oxygen saturation is not a sensitive measure of wound healing because hemoglobin delivery to the wound environment is disrupted by microvasculature damage, vasoconstriction, and clotting in the area surrounding a wound. However, the optical properties of tissue change measurably in this animal model during wound healing in contrast to the insignificant change of oxygen saturation. Therefore, tissue absorption coefficients may have adequate sensitivity to be good global indicators of changes during wound healing.

Discussion

In the NIR region, the change of the absorption coefficient $\mu_a$ reflects the variation in oxygenated and deoxygenated hemoglobin concentration because hemoglobin is the main absorption chromophore at the wavelength range 680-870 nm along with water and lipids. The NIR absorption coefficient during wound healing (FIG. 18) increases on the wound side by 0.020-0.035 cm$^{-1}$, and total hemoglobin concentration increases by 0.06-0.07 mM (FIG. 20). This means that during normal healing the optical properties of tissue change measurably in this animal model as a result of a 30-35% difference in blood volume between the wound side and the control side. It would be important to monitor how the absorption coefficient returns to normal levels (pre-wound) after the tissue has remodeled fully and the system recovered from the wound perturbation.

The experimental results demonstrating baseline differences $\mu_a$ between the left and right dorsal side highlight the importance of selecting a control site with well-understood optical properties relative to the wound site, and that a contralateral position may not be the optimal control site. In a clinical application, optical measurements occur on patients with already existing wounds. Therefore, trends of absorption and scattering coefficients of the wound sites should be looked at over time. Since it will be not be possible to compare the optical properties of patient wounds to any pre-wound baseline, in the clinic it is desirable to select a control site with stable optical properties. The optical properties of this control site will be used to establish the baseline stability of the human study described below. In the framework of the experimental model, the absorption coefficient should decrease if proper healing is occurring, as demonstrated in FIG. 22, which illustrates a hypothesized clinical wound healing curve. The dark solid lines represent the result of the animal study shown in FIG. 18, while the other lines are hypothesized curves for healing and non-healing wounds. The amount of time required for the healing curve to converge to the baseline is not known.

Figure 23:
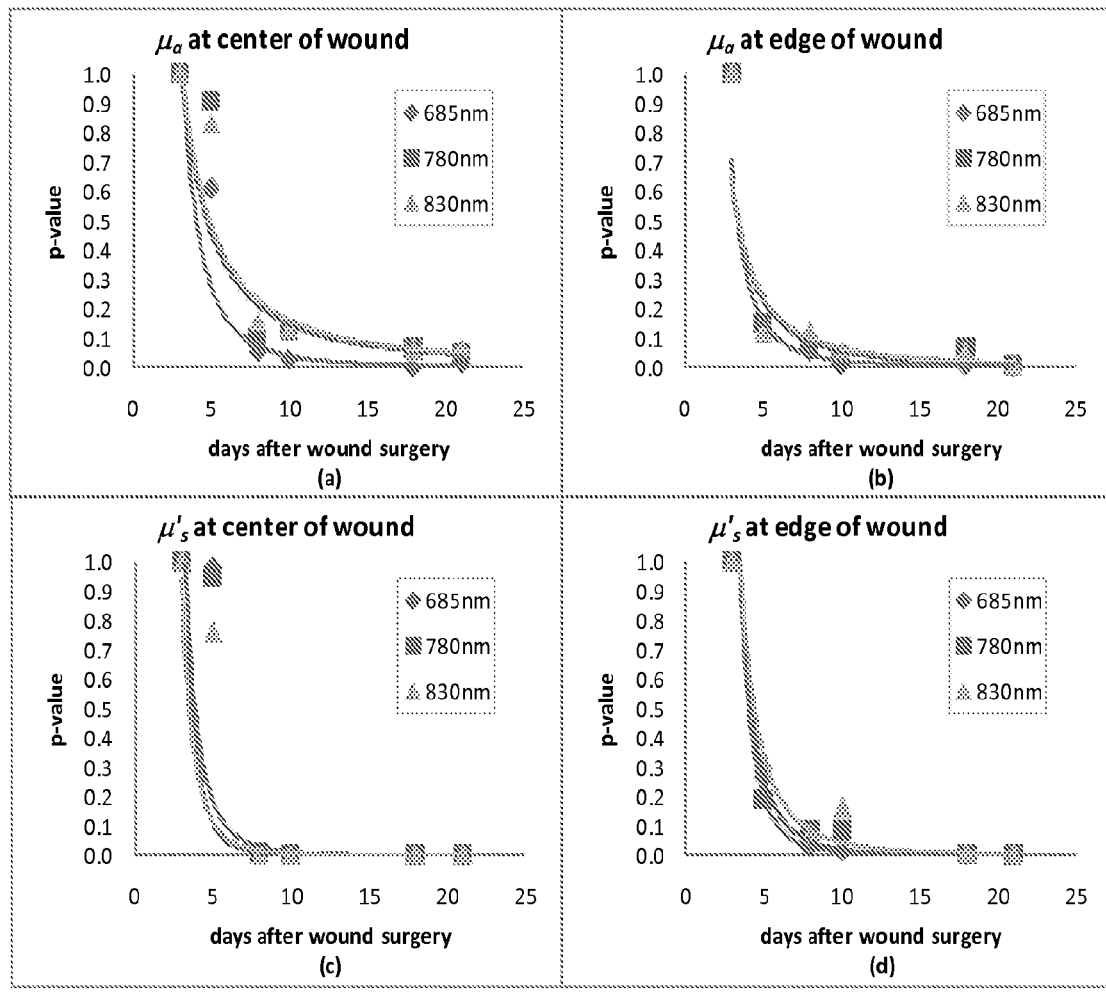
FIG. 23 illustrates two-tailed, unpaired t-tests used to compare the average optical coefficients at each time point to the average optical coefficients on day 3 where the resulting p-values are shown as a function of time. (a) $\mu_a$ at center of wound, (b) $\mu_a$ at edge of wound, (c) $\mu_s'$ at center of wound, and (d) $\mu_s'$ at edge of wound.

In order to further analyze the experimental results, two-tailed t-tests were performed to understand how the optical data reflect the process of wound healing in this animal model. The t-test allows differentiation of values of absorption and scattering over time with statistical significance and finer detail compared to a simple comparison of average values and their standard deviations. Absorption and scattering coefficients from day 3 of wound healing were compared to data from each subsequent timepoint using t-tests. The results, presented in FIG. 23, show that the p-value obtained for the 685 nm absorption coefficient becomes very small (at the level of 0.01) at day 18 for the wound center and at day 8 for the wound edge. FIG. 23 illustrates two-tailed, unpaired t-tests that were used to compare the average optical coefficients at each time point to the average optical coefficients on day 3. The resulting p-values are shown as a function of time for (a) $\mu_a$ at center of wound, (b) $\mu_a$ at edge of wound, (c) $\mu'_s$ at center of wound, and (d) $\mu'_s$ at edge of wound. The absorption at 685 nm is due mostly to deoxygenated hemoglobin corresponding to the tissue metabolic activity. Therefore, at the wound center there may be a time lag for significant metabolic activity. At the other two wavelengths 785 nm and 830 nm, the p-values are systematically higher demonstrating that 685 nm absorption may be a more sensitive indicator of metabolic changes that occur during wound healing than absorption at other wavelengths and oxygen saturation. Another very important conclusion from these data is that the p-value decreases earlier for the wound edge than it does for the wound center. These results are in agreement with a healing wound model where healing starts from the edges and the wound heals by contraction. This is the wound healing mode followed by this animal model where healing starts from "around" the wound, with increased metabolic activity and the wound center is the last location where epithelialization (new skin) is formed.

The demonstrated baseline stability of the device makes possible to use this method in a clinical setting where measurements are performed on chronic wounds spanning periods of 6-12 months. The results suggest that the NIR methodology and instrument developed by the inventors is stable and capable of detecting changes to optical properties connected to wound healing. This quantitative non-invasive method could complement the current practice of monitoring wound healing based on visual observation and measurement of wound size to improve the quality of wound care, particularly for chronic wounds due to diabetes, pressure ulcers (bed sores), venous ulcers, ubiquitous ulcers, ischemia, etc. Moreover, the method of the invention permits the identification of pressure ulcers, venous ulcers, and the like that would not otherwise be visible to upon visual examination of the wound.

In summary, the in vivo studies using the hairless rat animal model have demonstrated that the absorption coefficient of tissue at all NIR wavelengths probed (680, 785, 830) is higher in the wound compared with the unwounded side of animals, corresponding to increased vascularization. The observed differences in $\mu_a$ between the wounded and unwounded side of animals can be attributed to the traditional chromophores of oxygenated and deoxygenated hemoglobin, because no evidence of a different type of tissue chromophore in these wavelengths was found. The results also demonstrate that the right and left side of these animals are slightly asymmetric in their optical properties and this should be further explored for long term wound healing studies. As in the previous embodiment, the data gathering technique described above may be used to monitor values that may be, in turn, correlated to the healing state of the wound to, for example, enable a researcher to study the healing process and any mechanisms that interfere with the healing process. The healing state of the wound also may be used to determine whether any diagnosis or treatment are necessary.

Human Data

Materials and Methods

Near Infrared Instrumentation

A frequency domain near infrared instrument of the type described by Papazoglou et al. in "Optical properties of wounds: diabetic versus healthy tissue," IEEE Trans. Biomed. Eng., 2006, 53(6), pages 1047-55, was used. An optical fiber was used to deliver intensity modulated light (70 MHz) to the tissue from three diode lasers ($\lambda$=685, 780, and 830 nm). Four optical fiber bundles were used to deliver backscattered light from the tissue to avalanche photodiode (APD) detectors and quadrature (I/Q) demodulators. The I and Q signals in each detector were measured; these were determined by the attenuated amplitude and phase shift of the registered scattered light. All optical fibers were immobilized on a Teflon probe, with the four detector fibers fixed at distances of 4, 8, 12, and 16 mm from the source fiber.

It is known by those skilled that absorption and scattering coefficients of tissue may be calculated from the amplitude and phase shift of scattered NIR light using the diffusion approximation if the probe has a minimum distance between source and detector fibers greater than a couple transport mean free paths. The transport mean free path (l*) represents the distance of propagation of a collimated beam of light before it becomes effectively isotropic, and can be approximated by $1/\mu_s'$ when $\mu_s' \gg \mu_a$, as is the case in tissue. After propagating more than approximately a couple transport mean free paths, most photons have undergone multiple light scattering (i.e., they are now at a different orientation from their incident direction) and may be described as diffuse. Values of $\mu_s'$ in human skin at wavelengths of 685-830 nm typically range from 5-20 cm$^{-1}$; therefore, the transport length l* ranges from approximately 0.5 to 2 mm, since l* is the inverse of the reduced scattering coefficient $\mu_s'$. This suggests that the smallest source-detector distance that can be used in probe design for the diffusion approximation to be valid would be 2-4 mm. The probe used by the inventors has a minimum distance between source and detector fibers of 4 mm and therefore is within the diffusion approximation regime. Closed analytical solutions to the diffusion equation have been derived for semi-infinite measurement geometries that are typical of noninvasive tissue measurements, when sources and detectors are placed on an air-tissue interface and the optical fiber source is modeled as an isotropic, point light source. The final equations describing the absorption and scattering coefficients from measurements of light intensity and phase shift as a function of the source-detector separation distance are included in the afore-mentioned article by Papazoglou et al.

Figure 24:
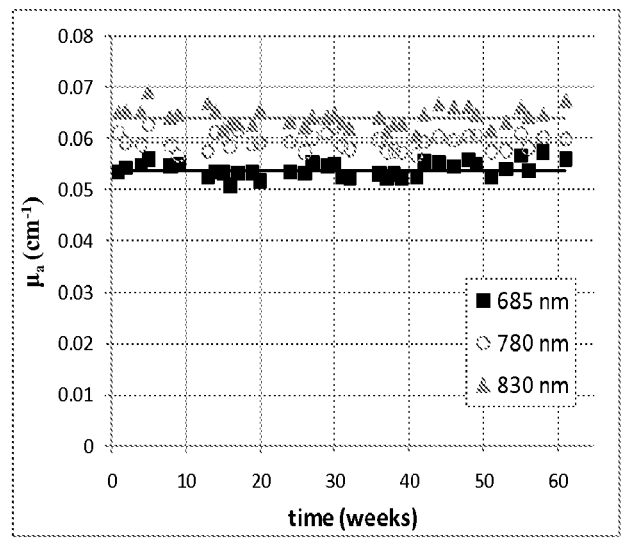
FIG. 24 illustrates daily average values of $\mu_a$ in a silicone optical phantom over a 61-week period.

The human study lasted for over a year and it was therefore necessary to test the stability of the device during the course of such measurements. To accomplish this, an optical phantom made of silicone (XP565—Silicones, Inc.) with dispersed particles of $TiO_2$ (diameter 0.9 to 1.6 µm—Alfa Aesar) to act as scatterers and carbon black acetylene (50% compressed, diameter 0.042 µm—Alfa Aesar) to absorb light was measured before each patient measurement session. The measured absorption coefficients from the silicone phantom over the course of 61 weeks are shown in FIG. 24. In particular, FIG. 24 illustrates daily average values of $\mu_a$ in a silicone optical phantom over a 61-week period. Each point represents the average of measurements taken on the same day. Solid lines represent average values for the entire measurement period. Standard error remained at less than 3% throughout the period of the study.

Oxyhemoglobin concentration ([$HbO_2$]) and deoxyhemoglobin concentration ([Hb]) were calculated from the measured values of $\mu_a$ by minimizing the difference between expected and measured absorption of tissue at these wavelengths (the left and right sides of the following equation):

$$\epsilon_{Hb}^{\lambda}[Hb]+\epsilon_{HBO2}^{\lambda}[HbO_2]+\mu_{a,H2O}^{\lambda}[\% H_2O]= \mu_{a,measured}^{\lambda} \quad (1)$$

where $\epsilon_{Hb}^{\lambda}$ and $\epsilon_{HBO2}^{\lambda}$ are the molar extinction coefficients of deoxy- and oxyhemoglobin, $\mu_{a,H2O}^{\lambda}$ is the absorption coefficient of pure water at each wavelength ($\lambda$), and the concentration of water [% $H_2O$] was assumed constant at 70%. The choice of a value for [% $H_2O$] has little effect on the calculated values of hemoglobin concentration because of the low absorption of water relative to hemoglobin at wavelengths in the range 685-830 nm. Total Hemoglobin Concentration [Tot Hb] was calculated as the sum of [Hb] and [$HbO_2$].

Human Subjects

Eleven subjects with diabetes and chronic wounds were recruited from the Drexel University Wound Healing Center in Philadelphia, Pa. All patients were between 18 and 65 years of age, had documented diabetes mellitus for at least 6 months, and had an ankle or foot wound with a minimum surface area of 1 cm$^2$ that was secondary to the complications of diabetes, including vascular disease and/or neuropathy. All patients received standard wound care, which included weekly or biweekly debridement, treatment with moist wound healing protocols, and offloading when appropriate. In some patients, active wound healing agents such as topical growth factors, hyperbaric oxygen, and bioengineered skin substitutes were employed. Details about the size of each wound, duration of measurements, and the active treatments used on each wound are shown in Table 1.

TABLE 1

Size, duration, and active treatments used on each wound

| Wound ID | Initial area (cm$^2$) | Final area (cm$^2$) | Number of weeks | Active treatment |
|---|---|---|---|---|
| Healing #1 | 6.1 | 0.1 | 10 | topical growth factor (Regranex) |
| Healing #2 | 1.2 | 0.0 | 10 | hyperbaric oxygen |
| Healing #3 | 4.5 | 0.0 | 14 | topical growth factor (Regranex) |
| Healing #4 | 4.5 | 0.2 | 14 | bioengineered skin substitute (Apligraf) |
| Healing #5 | 5.6 | 0.0 | 12 | topical growth factor (Regranex) |
| Non-healing #1 | 17.4 | 10.3 | 36 | bioengineered skin substitute (Dermagraft) |
| Non-healing #2 | 50.0 | 21.5 | 13 | none |
| Non-healing #3 | 15.6 | 11.3 | 30 | hyperbaric oxygen |
| Non-healing #4 | 14.1 | 3.2 | 61 | topical growth factor (Regranex) |
| Non-healing #5 | 74.5 | 17.7 | 16 | hyperbaric oxygen |
| Non-healing #6 | 31.5 | 13.8 | 32 | hyperbaric oxygen |
| Non-healing #7 | 16.2 | 4.5 | 15 | hyperbaric oxygen |

Of the 11 wounds enrolled in the study, five wounds healed completely in less than 15 weeks, three wounds resulted in amputation, and three wounds remained unhealed at the end of the study, as shown in Table 1. Four of the five healed wounds required no surgical intervention prior to closure, while one wound underwent surgical debridement and the application of a bioengineered skin substitute (Apligraf®, Organogenesis, Inc., Canton, Mass.) after 18 weeks of participation in the study and reached closure after an additional 17 weeks. Data obtained prior to surgical intervention were classified as a non-healing wound, while data obtained after surgery were classified as a healing wound, bringing the total number of wound to 12 (5 healing and 7 non-healing).

Figure 25:
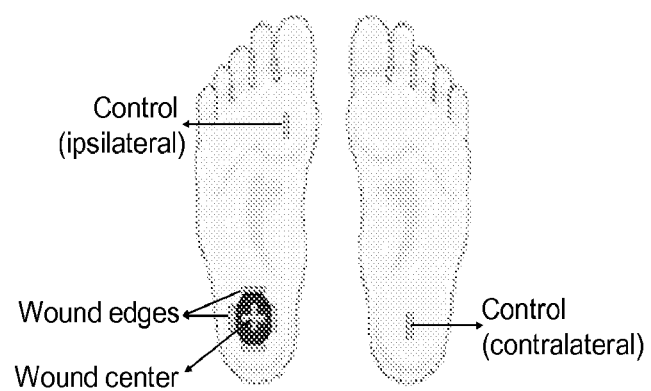
FIG. 25 illustrates the measurement locations for a typical diabetic foot ulcer in the human experiments.

All diffuse NIR measurements were conducted prior to wound debridement on a weekly or biweekly basis. During each measurement session, the wounds of each patient were interrogated using the NIR instrument in up to ten different locations. Measurement locations were chosen based on the geometry and size of each wound, and can be classified into four general locations: (1) directly on the wound, (2) on intact skin at the edge of the wound, (3) on non-wound tissue of the contralateral limb symmetric to the wound location if available, (4) on non-wound tissue on the ipsilateral limb at a distance of at least 2 cm from the wound. The NIR measurement locations for a typical diabetic foot ulcer are shown in FIG. 25. The dark oval on the heel of the right foot represents a typical diabetic foot ulcer. Gray rectangles represent the probe locations during a measurement session. Tegaderm transparent sterile dressing (3M Health Care) was used to cover the fiber optic probe during all measurements. The presence of Tegaderm has been found by the inventors to not affect the measured NIR coefficients.

Wounds were digitally photographed using a Fujifilm Finepix s700 digital camera during each measurement session with cross-polarizing filters to reduce surface reflection. Wound areas were calculated from the photographs using an image analysis code developed with Matlab (Mathworks, Inc.) software.

Results

Results from Diabetic Foot Ulcers

Figure 26:
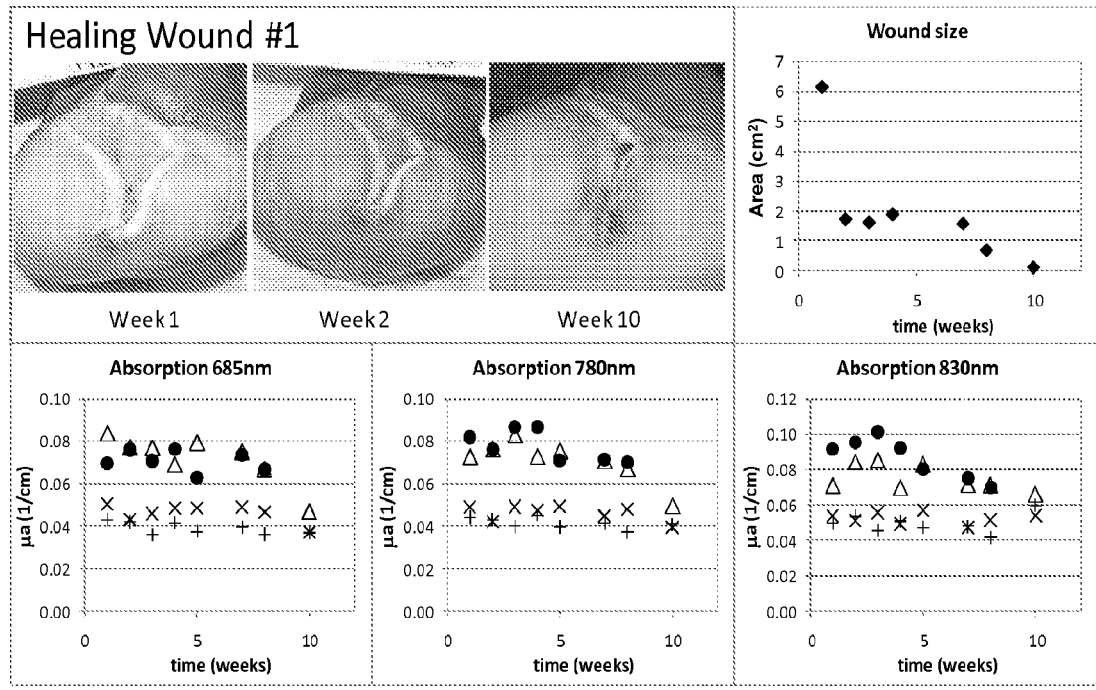
FIG. 26 illustrates plots of $\mu_a$ at all wavelengths during the course of the study for a typical healing wound.
Figure 27:
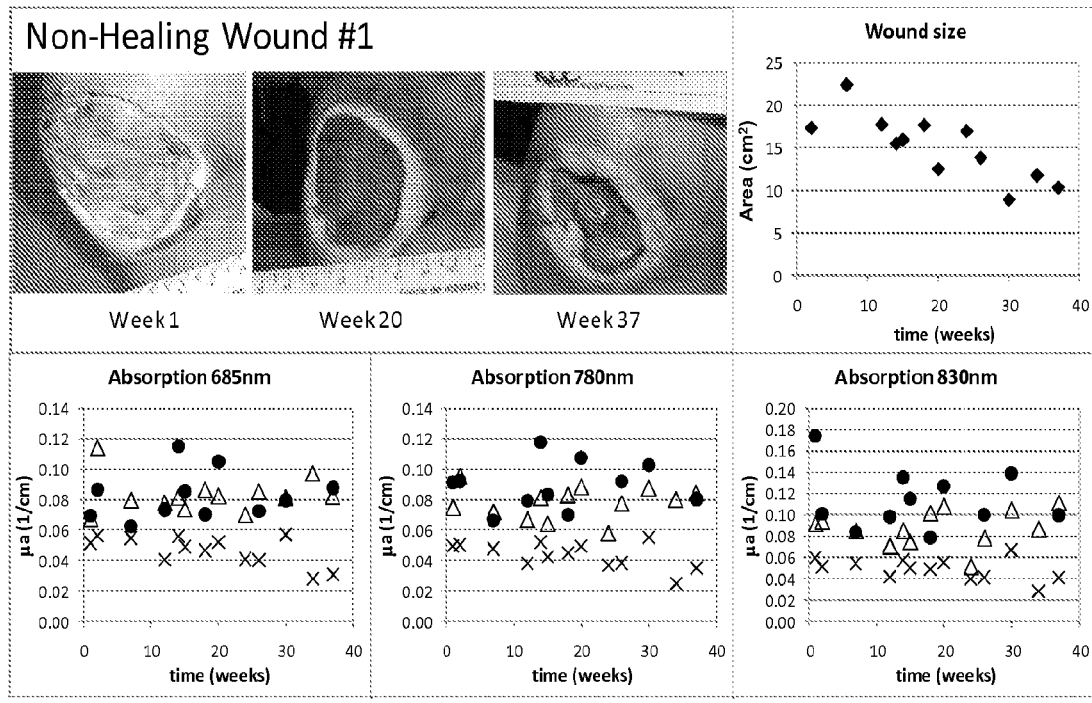
FIG. 27 illustrates plots of $\mu_a$ for a typical non-healing wound.
Figure 28:
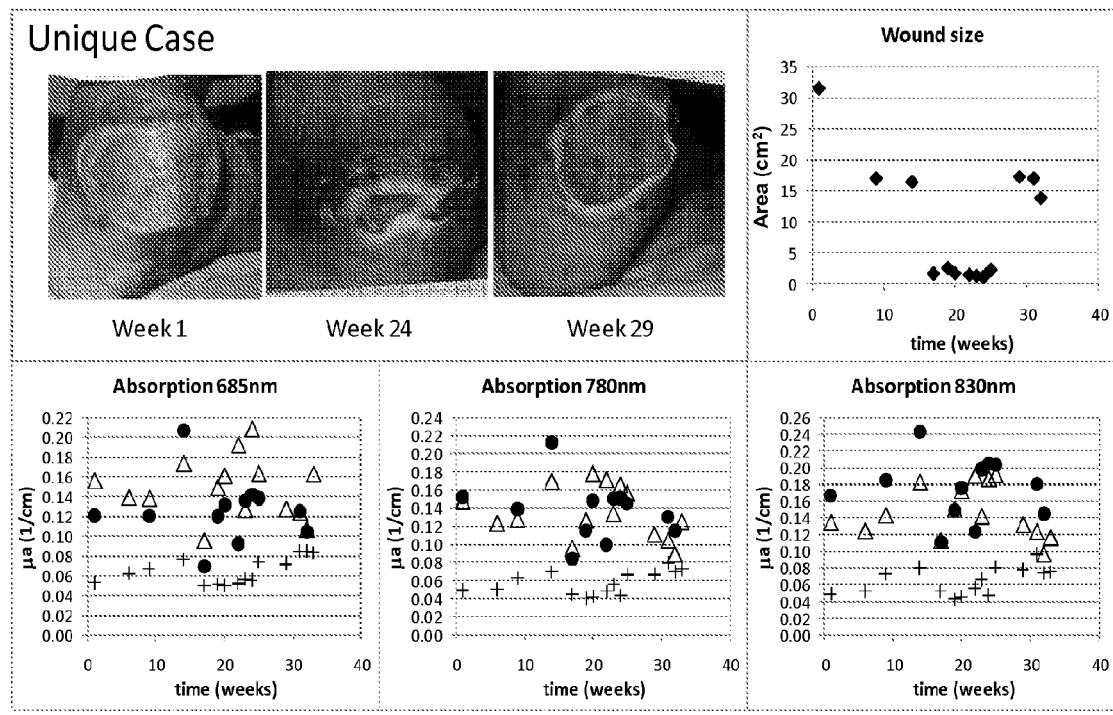
FIG. 28 illustrates plots of $\mu_a$ for a unique case in which the wound initially appeared to be healing, decreasing in size from 31.5 cm$^2$ to 1.6 cm$^2$ over 17 weeks but never closed completely and surgical intervention was required after week 25, increasing the wound size to 17.3 cm$^2$.

In both healing and non-healing wounds, values of the NIR absorption coefficient $\mu_a$ at the wound center and wound edges were greater than values of $\mu_a$ at the control (non-wound) sites. In all healing wounds the values of $\mu_a$ at the wound center and edge sites decreased and converged to the values measured at the control sites. This is illustrated in FIG. 26, which shows plots of $\mu_a$ at all wavelengths during the course of the study for a typical healing wound. FIG. 26 illustrates wound size, optical absorption, and hemoglobin data for a representative healed wound. In the upper left, digital photographs from selected time points are illustrated. In the upper right, wound area as determined through analysis of digital photographs (♦). In the lower sections, mean values of $\mu_a$ at 685 nm, 780 nm, and 830 nm are provided from each measurement day. Each data point represents the mean of measurements obtained from the center of the wound (●), the edges of the wound (Δ), a control site on the wounded foot (+), and a control site on the non-wounded foot (x). The area of this wound, which was located on the frontal region of a foot that had previously lost all toes to amputation, was over 6 cm$^2$ at the beginning of the study, and closed after ten weeks of monitoring. In contrast, values of $\mu_a$ in all non-healing wounds remained greater than the control sites and did not converge over the course of the study. This is illustrated in FIG. 27, which shows plots of $\mu_a$ for a typical non-healing wound with the same feature layout as in FIG. 26. A suitable control site on the wounded foot was unavailable due to the size of the wound and prior amputations. The area of this wound, which was located on the plantar metatarsal region of the foot, decreased by only approximately 50% over the course of 37 weeks, after which a below-the knee amputation was performed. FIG. 28 shows plots of $\mu_a$ for a unique case in which the wound initially appeared to be healing, decreasing in size from 31.5 cm$^2$ to 1.6 cm$^2$ over 17 weeks. FIG. 28 has the same feature layout as in FIGS. 26 and 27 but a suitable control site on the non-wounded foot was unavailable due to prior amputations. However, this wound, which was located on the plantar metatarsal region of the foot, never closed completely and surgical intervention was required after week 25, increasing the wound size to 17.3 cm$^2$. Despite a rapid decrease in wound size during the initial 17 weeks of the study, the NIR data from the wound site did not show convergence with the non-wound data as is characteristic of healing wounds in this study. This may indicate that the greater penetration depth achieved by diffuse NIR could provide clinicians with better assessment of wound status than superficial measurements of wound size.

Figure 29:
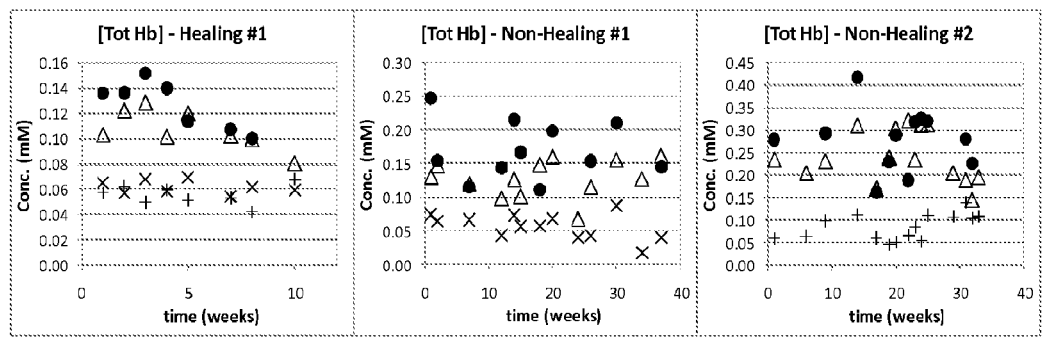
FIG. 29 illustrates the calculated values of total hemoglobin concentration [Tot Hb] for the wounds in FIGS. 26-28.

The calculated values of total hemoglobin concentration [Tot Hb] for the wounds in FIGS. 26-28 are shown in FIG. 29. In FIG. 29, mean values of total hemoglobin concentration from each measurement day are illustrated for healing wound #1 (left), non-healing wound #1 (center), and non-healing wound #2 (right). Each data point represents the mean of measurements obtained from the center of the wound (●), the edges of the wound (Δ), a control site on the wounded foot (+), and a control site on the non-wounded foot (x). As expected, the hemoglobin concentration trends are similar to those observed for optical absorption.

Rates of Change in Optical Data

Figure 30:
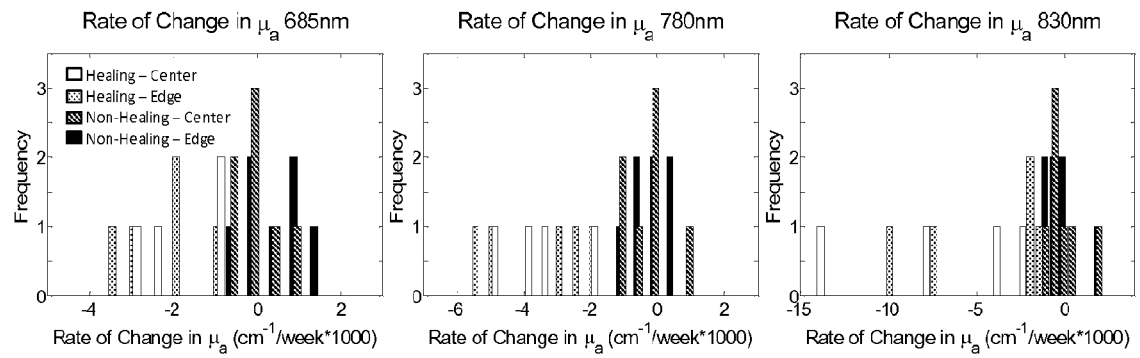
FIG. 30 illustrates the slopes calculated from the optical absorption trend lines.
Figure 31:
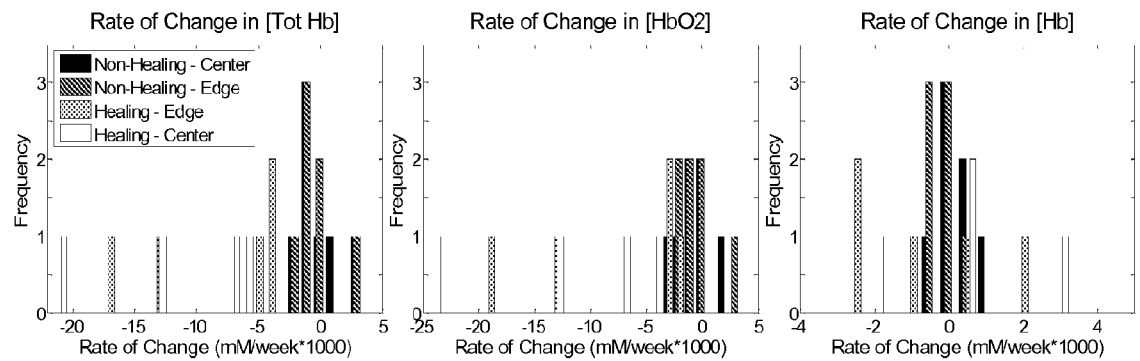
FIG. 31 illustrates the slopes calculated from the hemoglobin concentration trend lines.
Figure 32:
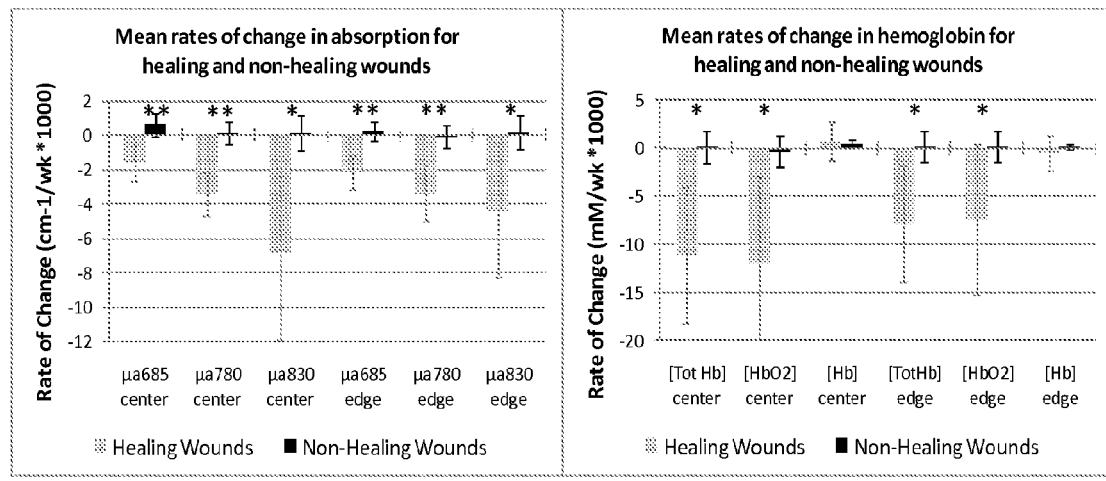
FIG. 32 illustrates the mean rates of change in healing and non-healing wounds compared for all optical absorption coefficients ($\mu_a$ at 685 nm, 780 nm, and 830 nm) and all hemoglobin concentrations ([Tot Hb], [HbO$_2$], and [Hb]).

In order to analyze the clinical data, the inventors identifies common parameters that describe the observed trends and that are representative of the clinical outcomes. In particular, the rate of temporal change of the absorption coefficient at each wavelength as well as the rate of temporal change in hemoglobin concentration can be estimated by fitting the data from each wound to a linear trend line. The limited amount of experimental data collected during this study combined with the data accuracy did not allow use of a more complicated fitting model at this time. The slopes of the trend lines were found to correspond to the rates of change in optical properties with time, and have proven useful in quantifying the progress of a healing wound. The slopes calculated from the optical absorption and hemoglobin concentration trend lines are referred to herein as the rates of change in each wound, and are shown in FIGS. 30 and 31, respectively. Rates of change in optical absorption for all wounds are shown in FIG. 30 at wavelengths left: 685 nm, center: 780 nm, and right: 830 nm. Similarly, rates of change in hemoglobin concentration for all wounds are shown in FIG. 31 at Left: Total hemoglobin concentration, center: Oxy-hemoglobin concentration, and right: Deoxy-hemoglobin concentration. White bars represent data from the centers of healing wounds; light gray bars represent data from the edges of healing wounds; dark gray bars represent data from the edges of non-healing wounds; black bars represent data from the centers of non-healing wounds. In all healing wounds negative rates of change were observed for the optical absorption coefficient at each wavelength, the total hemoglobin concentration, and the oxy-hemoglobin concentration. In all non-healing wounds the rates of change for the above properties were close to zero or slightly positive. The rate of change for deoxy-hemoglobin concentration was close to zero in both healing and non-healing wounds. The mean rates of change in healing and non-healing wounds are compared for all optical absorption coefficients ($\mu_a$ at 685 nm, 780 nm, and 830 nm) and all hemoglobin concentrations ([Tot Hb], [HbO$_2$], and [Hb]) in FIG. 32. In FIG. 32, error bars represent standard deviation. One-tailed, heteroscedastic t-tests were used in FIG. 32 to test the difference between the rates of change in healing and non-healing wounds, where *p<0.05 **p<0.01. As illustrated in FIG. 32, a statistically significant difference between the slopes of healing and non-healing wounds was obtained for the optical absorption coefficients at each wavelength, the total hemoglobin concentration, and the oxy-hemoglobin concentration.

Statistical Characterization of Healing and Non-Healing Wound Data

Figure 33:
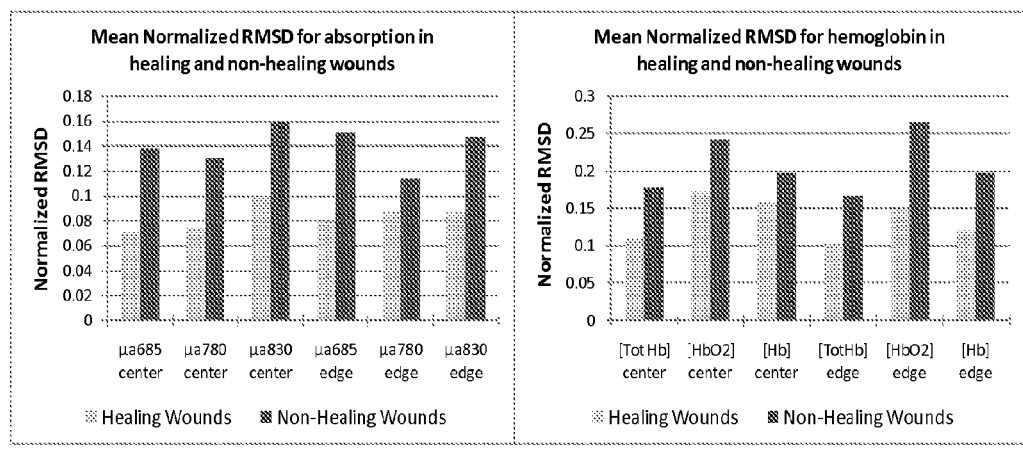
FIG. 33 compares the mean values of normalized RMSD in healing and non-healing wounds using the optical absorption at each wavelength and all hemoglobin concentrations (oxy, deoxy and total).

In addition to the rate of change of optical properties, the statistical characteristics of optical data from a wound may be an indicator of healing potential. Visual comparison of FIGS. 26-28 reveals more week-to-week variability in the non-healing data than in the healing data. To quantify variability differences, the root mean square deviation (RMSD) of experimental data from the fitted first-order polynomials was calculated. The RMSD values were normalized by dividing by the mean of the experimental values for each wound. FIG. 33 compares the mean values of normalized RMSD in healing and non-healing wounds using the optical absorption at each wavelength and all hemoglobin concentrations (oxy, deoxy and total). In FIG. 33, normalized RMSD of the lines are fitted to optical absorption (left) and hemoglobin concentration (right) data. The mean normalized RMSD was greater in non-healing wounds than in healing wounds for all absorption coefficients and hemoglobin concentrations.

Discussion

Figure 34:
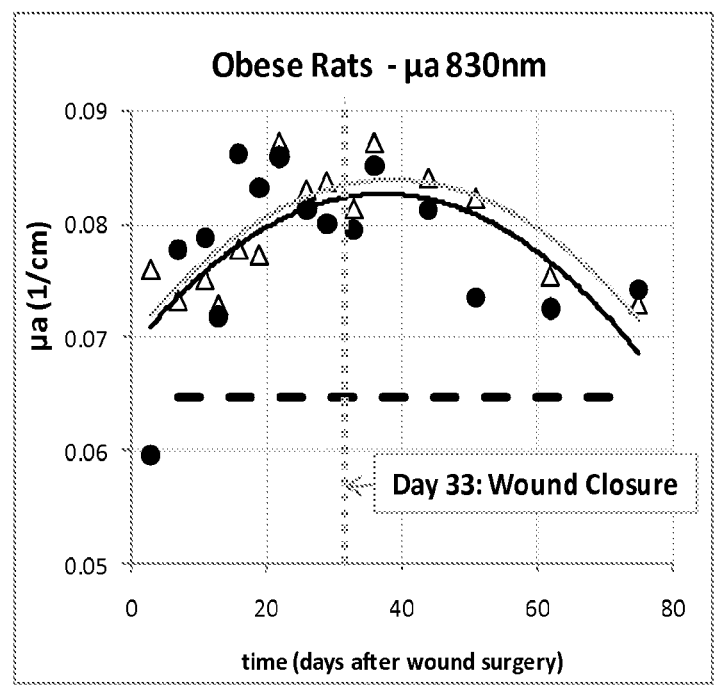
FIG. 34 illustrates the results of a study of wound healing in seven obese Zucker Diabetic Fatty (ZDF) rats in which the wounds were monitored using DPDW methodology throughout the healing cycle and for 42 days after wound closure.

The inventors have developed a hypothesized model of healing based on changes in the NIR optical properties of wounds related to vascularization that were verified by histopathology and immunohistochemistry. Specifically, results from the animal studies demonstrated increased optical absorption as blood volume increased in healing wounds. The inventors further hypothesized that if DPDW measurements were continued after closure of the wound, a decrease in optical absorption would be expected during the late proliferative phase of wound healing as vessel density/blood volume decreases to normal levels. This decrease have been confirmed in absorption through an unpublished pilot study of wound healing in seven obese Zucker Diabetic Fatty (ZDF) rats in which the wounds were monitored using DPDW methodology throughout the healing cycle and for 42 days after wound closure. The measured optical absorption coefficients at 830 nm behaved as expected, increasing prior to wound closure at day 33, and then gradually decreasing for the remaining 42 days of the study, as shown in FIG. 34. Each data point in FIG. 34 represents the mean of measurements obtained from the center of the wound (●, black line) and the edges of the wound (Δ, gray line).

Figure 35:
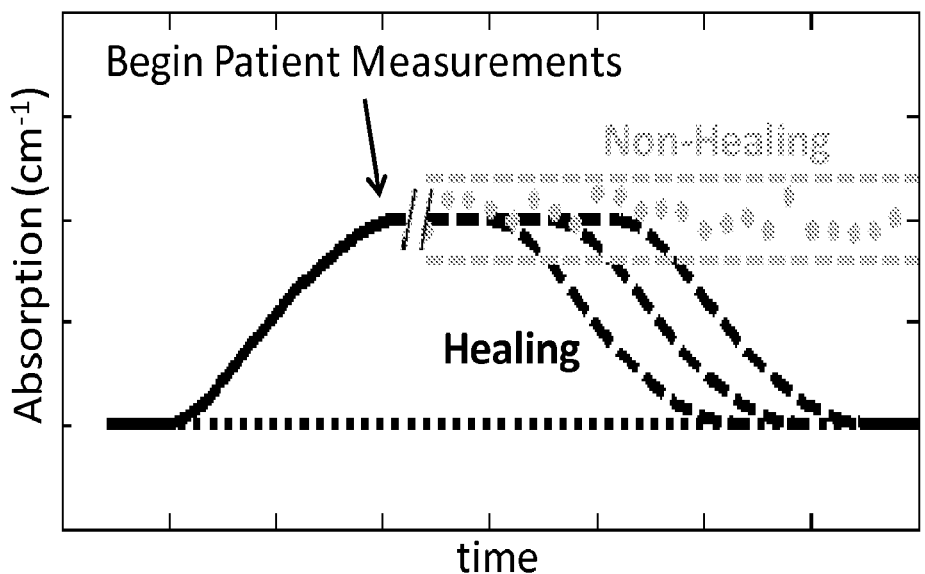
FIG. 35 illustrates a hypothesized model of the optical changes observed during healing.

A hypothesized model of the optical changes observed during wound healing is illustrated in FIG. 35. In FIG. 35, the dotted black line represents normal (non-wound) tissue, while the descending dashed black lines represent the hypothesized curve for healing wounds. The gray markers represent measurements on non-healing wounds. The time dependence of NIR optical absorption for human patients is expected to be different from that observed during the animal studies. Human patients are first seen when they have already developed chronic wounds, corresponding to an elevated yet constant absorption level (indicative of non-healing) in the healing model. Any progress in healing manifests itself by a decrease in the NIR absorption coefficient, and a convergence to the value of non-wound tissue (FIG. 35, dashed black lines). In wounds that do not heal, the level is not expected to converge with non-wound tissue (FIG. 35, gray markers). The rates of change in healing and non-healing wounds summarized in FIG. 32 are in agreement with the hypothesized healing model and may provide the basis for a quantitative "healing index" that helps clinicians to distinguish healing from non-healing wounds.

Figure 36:
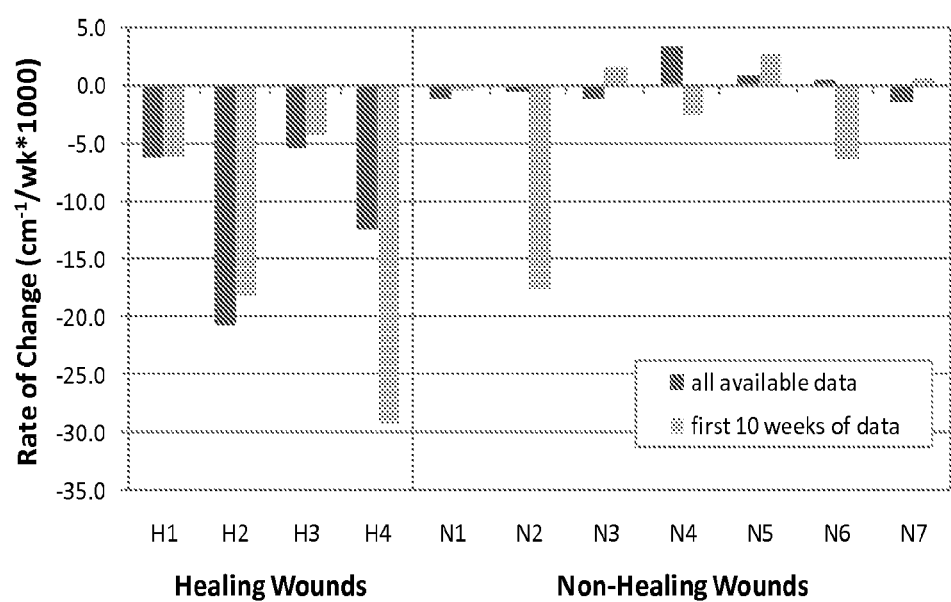
FIG. 36 illustrates the rate of temporal change of [Tot Hb] in each wound calculated by fitting the data from the first 10 weeks of measurements to a linear trend line, where the slopes of the 10-week trend lines are compared to the slopes calculated from all available data.

The predictive capability of a quantitative healing index derived from DPDW data may be confirmed through a study of more patients with measurements taken at more time points. As a first approximation, the rate of temporal change of [Tot Hb] in each wound was calculated by fitting the data from the first 10 weeks of measurements to a linear trend line. The slopes of the 10-week trend lines are compared to the slopes calculated from all available data in FIG. 36. In FIG. 36, rates of change in total hemoglobin concentration from the centers of all wounds are illustrated. Dark bars represent rates calculated using all available measurements; light bars represent rates calculated using the first 10 weeks of measurements available for each wound. If −0.003 cm$^{-1}$/wk is considered to be the threshold between a negative rate of change and a negligible rate of change, such that a negative rate of change predicts healing while a negligible rate of change predicts non-healing, 100% of the healing wounds are correctly classified (4 of 4) and 71% of the non-healing wounds are correctly classified (5 of 7). It is likely that the period of time needed to establish a predictive trend could be reduced if measurements were conducted more frequently. [Tot Hb] trends are evaluated using 10 weeks of data because on average each wound was measured 5.0 times during its first 10-week period, and 5 measurements appear to be adequate to establish a statistically adequate trend line. If DPDW measurements were conducted every week, it might be possible to establish a predictive trend line in only 5 weeks.

The rate of change of oxygenated hemoglobin concentration in healing wounds is greater than the rate of change in deoxygenated hemoglobin concentration, as shown in FIG. 31. During the late inflammatory/early proliferation stage of wound healing, angiogenesis increases the supply of oxygenated blood to the wound resulting in increased values of [$HbO_2$]. In the late proliferation stage, angiogenesis stops and blood vessels begin to break down as a result of apoptosis. The resulting decrease in supply of oxygenated hemoglobin to the wound may be reflected by the negative rate of changes of [$HbO_2$] observed in FIG. 31. Concentrations of deoxygenated hemoglobin reflect metabolic activity within the wound bed, and would be expected to remain relatively constant assuming that an adequate supply of oxygenated blood is being delivered to the wound. This could explain why the changes in [Hb] in healing wounds were less pronounced than changes in [$HbO_2$].

It has been hypothesized that chronic wounds (e.g., diabetic, pressure ulcer, venous ulcer, ubiquitous ulcer, and/or ischemic wounds) may be "stuck" in various phases of the healing process. The impaired (non-healing) wounds represented in FIGS. 27 and 28 may have been "arrested" before reaching the end of the proliferative phase of healing, resulting in oxygenated hemoglobin concentrations that were always greater than normal tissue and did not decrease like non-impaired (healing) wounds. Furthermore, there is evidence that neuropathy and a prolonged inflammatory response in diabetic patients are important factors in the etiology of diabetic foot ulcers. Diabetic neuropathy is associated with microcirculatory dysfunction in the foot, even in patients who have normal large-vessel blood flow to the foot. It has been hypothesized that repeated ischemia and reperfusion within the microvasculature of the foot may lead to cycles of inflammation in foot ulcers, further impairing the wound healing process. The high degree of week-to-week variability in non-healing wounds compared to healing wounds shown in FIG. 33 supports this hypothesis and could be an indication of cyclical changes in the microcirculation and inflammatory status of the wound.

In summary, temporal changes in the NIR optical properties of diabetic foot ulcers related to hemoglobin concentration can be measured using the techniques of the invention. Changes in the measured values may be used to monitor healing progress over time. These changes can be quantified by calculating the linear rate of change and the week to week variability in optical absorption coefficient and hemoglobin concentration over time. These metrics were used to distinguish healing (non-impaired) from non-healing (impaired) wounds in a study of human diabetic foot ulcers, indicating that DPDW methodology at near infrared wavelengths may be able to provide wound care clinicians with objective and quantitative data to help in the assessment of overall wound health when deciding on treatment options. In other words, the overall wound health may be used to determine whether any treatment is necessary. The nature of the treatment will depend on a number of factors including the nature of the wound, whether the patient is diabetic, the rate of healing of the wound, etc.

Those skilled in the art will appreciate that the near infrared (NIR) methodology disclosed herein probes tissue below the skin/wound surface at distances that depend upon the source fiber-detection fiber distance and range from 2 mm to several cm of tissue depth. Therefore, the optical properties of tissue can be assessed as well as the oxygenated and deoxygenated hemoglobin concentrations, and hence tissue oxygen saturation. This allows the method to be used in a variety of ischemic environments, caused by problems in blood supply or problems in oxygen supply to the affected area. All cases of impaired healing and subsurface compromised circulation can be assessed by the disclosed methodology. For example, emerging pressure ulcers (bed sores) or ubiquitous ulcers represent environments and tissue conditions that can be assessed by the NIR method. Surface imaging may not reveal problems underlying a pressure or bed ulcer before it surfaces, but impaired supply of blood and or oxygen which precedes such conditions can be non-invasively assessed by the NIR methodology described herein.

Those skilled in the art also will readily appreciate that many additional modifications are possible in the exemplary embodiments without materially departing from the novel teachings and advantages of the invention. For example, it is possible that modified simpler (e.g., continuous wave) or more complicated (e.g., time resolved) methods or modulation at higher frequencies of the frequency domain instrument can provide similar information as provided using the techniques described above. These and other obvious extensions are also included within the scope of the invention. Accordingly, any such modifications are intended to be included within the scope of this invention as defined by the following exemplary claims.

What is claimed:

1. A method of determining if a wound in a human patient is healing, comprising the steps of:
   illuminating the wound tissue in the patient with light from a light source;
   measuring over time less than ten weeks one or both of the amplitude and phase shift of the light as it propagates through the wound tissue; wherein the illuminating and measuring steps are performed using a diffuse photon density wave (DPDW) device that is a continuous wave, a frequency domain, or a time domain measurement device,
   calculating optical absorption coefficients using the measured amplitude or phase shift of the light;
   quantifying the concentration of the oxygenated hemoglobin or the total hemoglobin in the wound tissue over a period of time of less than ten weeks from the optical absorption coefficients; and
   determining the rate of change of the oxygenated hemoglobin or total hemoglobin concentration over the period of time, wherein a negative rate of change of either the oxygenated hemoglobin or total hemoglobin indicates the wound is healing and a negligible or positive rate of change indicates the wound is not healing.

2. The method of claim 1, wherein the light has a wavelength between 650 and 870 nm.

3. The method of claim 1, wherein the light has a near infrared wavelength selected from the group consisting of 685 nm light, 780 nm light, 830 nm light, and 950 nm light.

4. The method of claim 1, wherein the wound is selected from the group consisting of pressure ulcers, diabetic foot ulcers, ubiquitous ulcers, and venous ulcers.

5. The method of claim 1, further comprising differentiating a healing wound from a non-healing wound using the rate of change of total hemoglobin concentration over the period of time.

6. The method of claim 1, wherein the measurements are taken from at least 2 mm below the surface of the wound.

7. The method of claim 1, comprising determining the statistical variability of the measurements, wherein a higher degree of statistical variability between consecutive measurements relative to the variability in a healing wound indicates a non-healing wound.

8. The method of claim 1, wherein the period of time is less than five weeks.

9. The method of claim 1, wherein the concentration is measured up to five times over the period of time.

10. The method of claim 1, wherein the threshold between the negative rate of change and the negligible rate of change is a change of −0.003 cm$^{-1}$/wk in the optical absorption coefficient.

* * * * *